United States Patent
Sachs et al.

(10) Patent No.: US 10,238,451 B2
(45) Date of Patent: Mar. 26, 2019

(54) APPARATUS AND METHODS TO MODULATE BLADDER FUNCTION

(71) Applicant: Amphora Medical, Inc., Maple Grove, MN (US)

(72) Inventors: Dan Sachs, Minneapolis, MN (US); Edwin J. Hlavka, Minneapolis, MN (US)

(73) Assignee: Amphora Medical, Inc., Maple Grove, MN (US)

( * ) Notice: Subject to any disclaimer, the term of this patent is extended or adjusted under 35 U.S.C. 154(b) by 635 days.

(21) Appl. No.: 14/285,627

(22) Filed: May 22, 2014

(65) Prior Publication Data

US 2014/0257268 A1 Sep. 11, 2014

Related U.S. Application Data

(63) Continuation of application No. 14/030,869, filed on Sep. 18, 2013, now Pat. No. 9,095,351, which is a
(Continued)

(51) Int. Cl.
*A61B 18/14* (2006.01)
*A61B 18/04* (2006.01)
(Continued)

(52) U.S. Cl.
CPC .......... *A61B 18/1492* (2013.01); *A61B 18/04* (2013.01); *A61B 18/1477* (2013.01); *A61B 18/1485* (2013.01); *A61B 18/18* (2013.01); *A61B 18/1815* (2013.01); *A61B 18/24* (2013.01); *A61F 7/12* (2013.01); *A61B 2018/0022* (2013.01); *A61B 2018/00023* (2013.01); *A61B 2018/00083* (2013.01); *A61B 2018/00267* (2013.01); *A61B 2018/00517* (2013.01); *A61B 2018/00523* (2013.01);
(Continued)

(58) Field of Classification Search
CPC ........ A61B 2018/1861; A61B 18/1815; A61B 18/1485; A61B 18/1477
See application file for complete search history.

(56) References Cited

U.S. PATENT DOCUMENTS

| | | |
|---|---|---|
| 5,342,353 A | 8/1994 | Allen |
| 5,370,675 A | 12/1994 | Edwards |

(Continued)

FOREIGN PATENT DOCUMENTS

| | | |
|---|---|---|
| AU | 2010319333 B2 | 2/2014 |
| CN | 103764225 A | 4/2014 |

(Continued)

OTHER PUBLICATIONS

WIPO International Searching Authority, International Search Report and Written Opinion dated Jun. 24, 2015 in International Patent Application No. PCT/US2015/014500, 11 pages.
(Continued)

*Primary Examiner* — Michael Peffley
*Assistant Examiner* — Sean W Collins
(74) *Attorney, Agent, or Firm* — Fish & Richardson P.C.

(57) ABSTRACT

Apparatus and methods are provided to concentrate energy delivery in non-superficial target tissue within a trigone region of a human bladder wall to modulate bladder function.

15 Claims, 12 Drawing Sheets

Related U.S. Application Data continuation of application No. PCT/US2012/048419, filed on Jul. 26, 2012.

(60) Provisional application No. 61/511,776, filed on Jul. 26, 2011, provisional application No. 61/565,460, filed on Nov. 30, 2011.

(51) Int. Cl.
*A61B 18/18* (2006.01)
*A61F 7/12* (2006.01)
*A61B 18/24* (2006.01)
*A61B 18/00* (2006.01)

(52) U.S. Cl.
CPC ............... *A61B 2018/00577* (2013.01); *A61B 2018/143* (2013.01); *A61B 2018/183* (2013.01); *A61B 2018/1861* (2013.01)

(56) References Cited

U.S. PATENT DOCUMENTS

| | | | |
|---|---|---|---|
| 5,378,675 A | 1/1995 | Takeyama et al. | |
| 5,667,488 A | 9/1997 | Lundquist et al. | |
| 5,672,153 A | 9/1997 | Lax et al. | |
| 5,964,727 A | 10/1999 | Edwards et al. | |
| 6,091,995 A * | 7/2000 | Ingle .................... | A61N 1/403 606/41 |
| 6,129,726 A | 10/2000 | Edwards et al. | |
| 6,190,353 B1 | 2/2001 | Makower et al. | |
| 6,216,704 B1 | 4/2001 | Ingle et al. | |
| 6,231,518 B1 | 5/2001 | Grabek et al. | |
| 6,325,798 B1 | 12/2001 | Edwards et al. | |
| 6,419,653 B2 | 7/2002 | Edwards et al. | |
| 6,425,877 B1 | 7/2002 | Edwards | |
| 6,607,525 B2 * | 8/2003 | Franco .................... | A61B 18/20 604/20 |
| 6,610,054 B1 | 8/2003 | Edwards et al. | |
| 6,626,930 B1 | 9/2003 | Allen et al. | |
| 6,632,193 B1 | 10/2003 | Davison et al. | |
| 6,692,490 B1 * | 2/2004 | Edwards ............ | A61N 1/36007 606/41 |
| 6,852,091 B2 | 2/2005 | Edwards et al. | |
| 6,960,205 B2 | 11/2005 | Jahns et al. | |
| 7,818,039 B2 | 10/2010 | Jahns et al. | |
| 8,197,504 B2 | 6/2012 | Stokes | |
| 8,641,711 B2 | 2/2014 | Kelly et al. | |
| 8,657,814 B2 | 2/2014 | Werneth et al. | |
| 8,684,998 B2 | 4/2014 | Demarais et al. | |
| 8,721,632 B2 | 5/2014 | Hoey et al. | |
| 8,740,896 B2 | 6/2014 | Zarins et al. | |
| 8,758,337 B2 | 6/2014 | Skwarek et al. | |
| 8,771,267 B2 | 7/2014 | Kunis et al. | |
| 8,771,269 B2 | 7/2014 | Sherman et al. | |
| 8,790,281 B2 | 7/2014 | Diederich et al. | |
| 8,840,625 B2 | 9/2014 | Adams et al. | |
| 9,561,067 B2 | 2/2017 | Sharma | |
| 2002/0002372 A1 | 1/2002 | Jahns et al. | |
| 2002/0003244 A1 | 1/2002 | Tooher et al. | |
| 2002/0032441 A1 * | 3/2002 | Ingle .................... | A61B 18/1482 606/41 |
| 2002/0188169 A1 * | 12/2002 | Kammerer ......... | A61B 1/00087 600/30 |
| 2002/0193851 A1 | 12/2002 | Silverman | |
| 2003/0032860 A1 | 2/2003 | Avni et al. | |
| 2004/0021579 A1 | 2/2004 | Oursler et al. | |
| 2004/0059389 A1 | 3/2004 | Chornenky | |
| 2004/0153098 A1 | 8/2004 | Chin et al. | |
| 2004/0186468 A1 * | 9/2004 | Edwards ................ | A61B 1/32 606/41 |
| 2004/0215179 A1 * | 10/2004 | Swoyer .............. | A61B 18/1477 606/32 |
| 2006/0089635 A1 * | 4/2006 | Young ................. | A61B 18/148 606/41 |
| 2007/0014784 A1 | 1/2007 | Nayak | |
| 2007/0112340 A1 | 5/2007 | Thomas et al. | |
| 2009/0069803 A1 | 3/2009 | Starkebaum | |
| 2009/0171315 A1 * | 7/2009 | Versi .................... | A61K 9/0034 604/511 |
| 2010/0049186 A1 * | 2/2010 | Ingle ................. | A61B 18/1485 606/33 |
| 2010/0174306 A1 | 7/2010 | Mitelberg et al. | |
| 2010/0256446 A1 | 10/2010 | Raju | |
| 2011/0112434 A1 | 5/2011 | Ghabrial et al. | |
| 2011/0270243 A1 | 11/2011 | Skarda et al. | |
| 2012/0048417 A1 | 3/2012 | Smith | |
| 2012/0048419 A1 | 3/2012 | Giribona | |
| 2012/0123411 A1 | 5/2012 | Ibrahim et al. | |
| 2013/0018281 A1 | 1/2013 | Nagale | |
| 2013/0030249 A1 | 1/2013 | Vazales et al. | |
| 2013/0066308 A1 | 3/2013 | Landman | |
| 2013/0072855 A1 | 3/2013 | Sherry et al. | |
| 2013/0090640 A1 | 4/2013 | Nagale et al. | |
| 2013/0090648 A1 | 4/2013 | Nagale et al. | |
| 2013/0172864 A1 | 7/2013 | Ibrahim et al. | |
| 2014/0012247 A1 | 1/2014 | Bakos et al. | |
| 2014/0012256 A1 | 1/2014 | Deem et al. | |
| 2014/0018786 A1 | 1/2014 | Van Wyk et al. | |
| 2014/0025055 A1 | 1/2014 | Burnett et al. | |
| 2014/0031810 A1 | 1/2014 | Mahvi et al. | |
| 2014/0039356 A1 | 2/2014 | Sachs et al. | |
| 2014/0039491 A1 | 2/2014 | Bakos et al. | |
| 2014/0081257 A1 * | 3/2014 | Ghoniem ........... | A61B 18/1477 606/33 |
| 2014/0148798 A1 | 5/2014 | Sachs et al. | |
| 2014/0163548 A1 | 6/2014 | Christian | |
| 2014/0200568 A1 | 7/2014 | Sharma | |
| 2014/0207136 A1 | 7/2014 | De La Rama et al. | |
| 2014/0257272 A1 | 9/2014 | Clark, III et al. | |
| 2014/0276593 A1 | 9/2014 | Nagale et al. | |
| 2014/0276726 A1 | 9/2014 | Model | |
| 2016/0030107 A1 | 2/2016 | Herbst et al. | |

FOREIGN PATENT DOCUMENTS

| | | |
|---|---|---|
| CN | 102256560 B | 7/2014 |
| CN | 104080418 A | 10/2014 |
| EP | 2155093 B1 | 5/2011 |
| EP | 2349045 B1 | 7/2014 |
| EP | 2759276 A1 | 7/2014 |
| EP | 2813192 A2 | 12/2014 |
| JP | 2001/514921 | 9/2001 |
| JP | 2003/510126 | 3/2003 |
| JP | 2009/532074 | 9/2009 |
| JP | 2010/533036 | 10/2010 |
| WO | WO 2004/010843 A2 | 2/2004 |
| WO | WO2013016588 A1 | 1/2013 |
| WO | WO2013160772 A2 | 10/2013 |
| WO | 2014004698 A1 | 1/2014 |
| WO | 2014022379 A1 | 2/2014 |
| WO | 2014022436 A1 | 2/2014 |
| WO | 2014025394 A1 | 2/2014 |
| WO | 2014026028 A1 | 2/2014 |
| WO | 2014113724 A2 | 7/2014 |

OTHER PUBLICATIONS

Chinese Patent Office, Office Action dated Jan. 4, 2016 in Chinese Patent Application No. 201280046659.X, 21 pages.
WIPO International Searching Authority, International Search Report and Written Opinion dated Nov. 26, 2012 in International Patent Application No. PCT/US2012/048419, 17 pages.
WIPO International Searching Authority, International Search Report and Written Opinion dated Nov. 21, 2012 in International Patent Application No. PCT/US2012/048417, 16 pages.
WIPO International Searching Authority, International Search Report and Written Opinion dated Aug. 25, 2015 in International Patent Application No. PCT/US2015/032298, 10 pages.
International Search Report and Written Opinion in Application No. PCT/US2015/032298, dated Aug. 25, 2015, 10 pages.

(56) References Cited

OTHER PUBLICATIONS

Semmelink et al., Histomorphometric Study of the Lower Urogenital Tract in Pre- and Post-Menopausal Women, Cytometry 11:700-707 (1990).
WIPO International Searching Authority, International Search Report and Written Opinion dated Jun. 24, 2015, in Application No. PCT/US/2015/014500, 11 pages.

* cited by examiner

Section A-A

APPARATUS AND METHODS TO MODULATE BLADDER FUNCTION

RELATED APPLICATIONS

This application is a continuation of U.S. patent application Ser. No. 14/030,869 (now U.S. Pat. No. 9,095,351) filed Sep. 18, 2013 entitled Apparatus And Methods To Modulate Bladder Function; which is a Continuation Application of and claims priority to International Patent Application No. PCT/US2012/048419, International Filing Date 26 Jul. 2012, entitled Apparatus And Methods To Modulate Pelvic Nervous Tissue; which claims benefit of priority to U.S. Provisional Application Ser. No. 61/511,776 filed Jul. 26, 2011, and claims benefit of priority to U.S. Provisional Application Ser. No. 61/565,460 filed Nov. 30, 2011, all of which are hereby incorporated herein by reference in their entireties.

BACKGROUND

Urinary incontinence (UI) is the involuntary leakage of urine. There are several types of urinary incontinence, including urge urinary incontinence (UUI) and stress urinary incontinence (SUI). Urge urinary incontinence is the involuntary loss of urine while suddenly feeling the need or urge to urinate. Stress urinary incontinence, typically affecting females, is the involuntary loss of urine resulting from increased abdominal pressure, such as generated by physical activity, exercising, coughing, sneezing, laughing, lifting, etc. Mixed incontinence combines attributes of SUI and UUI.

Overactive bladder (OAB) is the strong, sudden urge to urinate, with or without urinary incontinence, usually with frequency and nocturia. The urge associated with overactive bladder can be assessed using the subjective experience of the patient, with or without any objectively verifiable metric, condition, behavior, or phenomena.

Historically, attempts have been made to translate the subjective patient experience of overactive bladder into a verifiable clinical test. Based upon work in spinal cord injury patients, it was hypothesized that the sensation of urgency and the result of urine leakage was due to non-volitional urinary bladder detrusor muscle contractions. Consequently, there was a push to implement urodynamic testing to observe and quantify the presumed detrusor contractions. However, the results found a poor correlation (e.g., 60%) between observed detrusor overactivity and the experience of urgency, and also found that asymptomatic individuals may exhibit detrusor contractions during urodynamic testing.

Given the limitations of urodynamic testing, the diagnosis and treatment decisions for overactive bladder transitioned to being assessed wholly by the patient's subjective experience. However, the detrusor muscle and its contractions are still considered to have a major role in overactive bladder.

Bladder control is a complex combination of voluntary and involuntary neurologic control, which responds to a highly distributed set of afferent (sensory) nerves associated with the bladder. Also, there is evidence of a myogenic origin for at least a portion of bladder wall contractile activity. While there are some descriptive hallmarks of idiopathic overactive bladder (e.g., thickened wall, characteristic "patchy" denervation, changes in smooth muscle and collagen morphology, increased electrical connectivity), there is no specific anatomic cause of OAB (e.g., a lesion, defect, injury, etc.), and also it is believed that there is no commensurate remedy for the cause. Neurogenic injury (e.g., spinal cord injury) and bladder outlet obstruction (BOO) can both lead to overactive bladder due to a chronic state of bladder inflation and a "high pressure" bladder. However, resolution of an outlet obstruction fails to rectify overactive bladder symptoms in a significant fraction (e.g., 25%) of these patients.

Overactive bladder affects at least 33 million patients in the United States alone, representing 16% of the adult United States population and roughly $12 billion dollars in healthcare cost. Overactive bladder and urinary incontinence significantly affect the quality of life and the ability of patients to maintain their lifestyle, including socializing, mobility, or independence. Further, urinary incontinence is one of the most common reasons for entering long-term care facilities, such as nursing homes, and is also a significant risk factor for injury due to falls resulting from hurrying to the toilet in response to urge.

Referring to FIGS. 1-3, the anatomy of the female bladder is described to provide context for discussion of previously-known treatment modalities, and is illustrative of why a significant unmet need for improved treatment modalities remains. In particular, FIG. 1 depicts a lateral sectional of the anatomical structures of a bladder (B) and a urethra (U), while FIG. 2 depicts an anterior sectional view of the bladder and urethra. FIGS. 1-2 further illustrate a trigone (T), ureteral ostium (O) (also referred to as a ureteral orifice), detrusor muscle (D), a neck (N), an interureteric crest (C), a fundus (F), and a body (BB).

FIG. 3 depicts a cross sectional view of a wall of the bladder, including an intravesical region (IR) (also referred to as the cavity), mucous membrane (also referred to as the mucosa), lamina propria (LP), muscularis propria (MP), adventitia (A), and perivesical fat (PF). The mucous membrane lines the intravesical region (IR) of the bladder and includes a three-layered epithelium, collectively referred to as transitional cell epithelium (TCE) or urothelium, and basement membrane (BM). The three layers of the transitional cell epithelium include the basal cell layer, the intermediate cell layer, and the surface cell layer. The basal cell layer can renew the transitional cell epithelium by cell division. New cells can migrate from the basal layer to the surface cell layer, and the surface cell layer can be covered by glycosaminoglycan (GAG) layer (GL). The function of GAG layer is controversial, possibly serving as an osmotic barrier or even an antibacterial coating for transitional cell epithelium. The basement membrane is a single layer of cells that separates transitional cell epithelium from the lamina propria.

Lamina propria (also referred to as the submucosa or suburothelium) is a sheet of extracellular material that may serve as a filtration barrier or supporting structure for the mucous membrane and includes areolar connective tissue and contains blood vessels, nerves, and in some regions, glands. Muscularis propria (also referred to as the detrusor muscle or the muscle layer) may be interlaced with lamina propria and may have three layers of smooth muscle, the inner longitudinal, middle circular, and outer longitudinal muscle.

When the bladder is empty, the mucosa has numerous folds called rugae. The elasticity of rugae and transitional cell epithelium allow the bladder to expand as the bladder fills with fluid. The thickness of the mucosa and muscularis propria can range between approximately 2 to 5 mm when the bladder is full and between approximately 8 to 15 mm when the bladder is empty.

The outer surface of muscularis propria may be lined by adventitia A about the posterior and anterior surface of the bladder or by the serosa about the superior and upper lateral surfaces of the bladder. Perivesical fat (PF) can surround the bladder outside of the serosa or adventitia. In some cases, a variety of fascia layers may surround or support the organs of the pelvis. Collectively, the fascias near the urinary bladder can be referred to as perivesical fascia.

A number of therapies have been developed for treating overactive bladder, including delivery of anticholinergic drugs, bladder retraining, sacral nerve stimulation (SNS), intravesical drug infusions, surgical denervation procedures, surgeries to increase bladder volume (e.g., detrusor myomectomy, augmentation cystoplasty) and botulinum toxin (e.g., Botox®, Dysport®, etc.) injections into the bladder wall. Each of these therapies has drawbacks, as described below.

Anticholinergic drugs, used alone or in combination with traditional nonsurgical approaches, such as bladder retraining, Kegel exercises, biofeedback, etc., often is used as first-line therapy for overactive bladder; however, the mode of action is uncertain. Anticholinergic drug use was initially thought to decrease contractions of the detrusor muscle during the filling stage (e.g., detrusor muscle overactivity, unstable detrusor muscle, etc.). However, it is now believed that anticholinergic drugs may not change detrusor muscle contractility, but instead modulate afferent (e.g., cholinergic) nervous traffic to the central nervous system.

Efficacy of anticholinergic drugs is generally quite modest, as approximately 50% of patients find such therapy subjectively inadequate. A reduction of 10% to 20% in the number of micturations per day (e.g., from 11 micturations to 9 micturations) and a reduction of 50% in urinary incontinence episodes (e.g., from 2 per day to 1 per day) is typical. However, these effects are frequently inadequate to significantly improve patient quality of life (QOL). Many patients would not even notice a change of 2 micturations per day unless they are keeping a log for a formal study. The remaining urinary incontinence episodes, although slightly less in number, continue to maintain the stigma and lifestyle limitations of the disease, such as the inability to travel or to be active, social withdrawal, etc. In addition, anticholinergic drugs can have side effects, including dry mouth, constipation, altered mental status, blurred vision, etc., which may be intolerable, and in many instances outweigh the modest benefits attained. Approximately 50% of patients abandon anticholinergic therapy within 6 months.

Sacral nerve stimulation (SNS) has a higher level of efficacy (e.g., up to 80% in well-selected and screened patients), but here too the mode of action is not well understood. The clinical benefit of SNS for urinary incontinence was a serendipitous finding during clinical trials of SNS for other conditions. The SNS procedure has a number of drawbacks: it is expensive and invasive, and requires surgery for temporary lead placement to test for patient response, followed by permanent lead placement and surgical implantation of a pulse generator in patients who responded favorably to the temporary lead. Regular follow-ups also are required to titrate SNS stimulation parameters, and battery replacements are necessary at regular intervals.

A variety of surgical denervation or disruption procedures have been described in the literature, but most have showed poor efficacy or durability. The Ingelman-Sundberg procedure, first developed in the 1950s and described in Ingelman-Sundberg, A., "Partial denervation of the bladder: a new operation for the treatment of urge incontinence and similar conditions in women," Acta Obstet Gynecol Scand, 38:487, 1959, involves blunt surgical dissection of the nerves feeding the lateral aspects of the bladder near its base. The nerves are accessed from the anterior vaginal vault, with the dissection extending bilaterally to the lateral aspect of the bladder. The denervation process is accomplished somewhat blindly, using blunt dissection of the space and targeting the terminal pelvic nerve branches. Although capable of producing promising results, the procedure as originally proposed entails all of the drawbacks and expense normally associated with surgical procedures.

McGuire modified the Ingelman-Sundberg procedure in the 1990s, as described in Wan, J., et al., "Ingelman-Sundberg bladder denervation for detrusor instability," J. Urol., suppl., 145: 358A, abstract 581, 1991, to employ a more limited and central dissection within the serosal layer of the bladder, staying medial to the vaginal fornices. Surgical candidates for the Modified Ingelman-Sundberg procedure can be screened to isolate likely "responders" using sub-trigonal anesthetic injections. As reported in 1996 by Cespedes in Cespedes, R. D., et al., "Modified Ingelman-Sundberg Bladder Denervation Procedure For Intractable Urge Incontinence," J. Urol., 156:1744-1747 (1996), 64% efficacy was observed at mean 15 month follow-up following the procedure. In 2002, Westney reported in Westney, O. L., et al., "Long-Term Results Of Ingelman-Sundberg Denervation Procedure For Urge Incontinence Refractory To Medical Therapy," J. Urol., 168:1044-1047 (2002), achieving similar efficacy at mean 44 month follow-up after the procedure. More recently, in 2007, Juang reported in Juang, C., et al., "Efficacy Analysis of Trans-obturator Tension-free Vaginal Tape (TVT-O) Plus Modified Ingelman-Sundberg Procedure versus TVT-O Alone in the Treatment of Mixed Urinary Incontinence: A Randomized Study," E. Urol., 51:1671-1679 (2007), using a combination of a transvaginal tape (TVT) sling (the "gold standard" surgical therapy for stress incontinence) and the Modified Ingelman-Sundberg procedure for mixed incontinence patients and showed a significant benefit for including the Modified Ingelman-Sundberg procedure, over the TVT sling alone, out to 12 months follow-up following the procedure.

Despite its clinical success, however, the Modified Ingelman-Sundberg procedure has not been widely adopted, as it is highly invasive and requires general anesthesia. Further, the terminal nerve branches are not visible to a surgeon, and thus, the dissection must be performed using approximate anatomical landmarks rather than using direct visualization of target nerve branches. Possible complications of the Modified Ingelman-Sundberg procedure include the risks associated with anesthesia, blood loss, vaginal numbness or fibrosis, adhesions, fistulas, vaginal stenosis, wound infection, or dyspareunia (pain with intercourse). Perhaps most importantly, efficacy of the Modified Ingelman-Sundberg procedure may be dependent upon surgical skill and technique.

More recently, another therapy involving injection of botulinum toxin (e.g., Botox®) into the bladder wall has been developed to address the symptoms of overactive bladder by blocking nerve traffic and causing temporary muscle paralysis following injection. During the injection procedure, which may be performed in a physician's office under local anesthesia, a cystoscope is introduced into the bladder through the urethra and a number of separate needle injections (e.g., 20-30) are made into the bladder wall. Initially the trigone, the area of the bladder defined by the ostia of the two ureters and the urethra, was avoided due to concerns about procedural pain due to dense afferent innervation of the trigone region and the potential for vesicoureteral reflux. However, the trigone region has more recently been included, and sometimes specifically targeted to the exclusion of the dome of the bladder. Initially, botulinum toxin was assumed to act only on the efferent motor nerves (e.g., causing partial paralysis of the detrusor muscle). More recent research indicates that botulinum toxin may have an effect on afferent sensory nerves as well. U.S. Pat. No. 8,029,496 to Versi provides an example of a system for delivering such a therapeutic agent to the trigone of the bladder through the vaginal wall.

Typically, botulinum toxin injections achieve a fairly high level of efficacy (e.g., resolution of symptoms), with maximum changes in cystometric capacity peaking at 4 weeks and complete continence being achieved in about half of patients. However, botulinum toxin does carry with it the risks of systemic effects, such as flu-like symptoms, nausea, weakening of respiratory muscles, transient muscle weakness, allergic reaction, or developed sensitivity. Other adverse events associated with botulinum toxin injections include acute urinary retention (AUR), large postvoid residual volume (PVR), difficulty in urination ("straining"), and urinary tract infection (UTI). Challenges with botulinum toxin therapy include procedural skill (e.g., dexterity with cystoscope and needle), uncontrolled drug diffusion, variable needle penetration depth, and reproducibility of technique. In addition, the effects of botulinum toxin wear off with time, typically after 6-9 months, requiring repeat injections for the lifetime of the patient.

Stress urinary incontinence, typically affecting females, is an anatomic issue where the pelvic floor has been damaged and weakened, such as during childbirth. Here, front line therapies are conservative (e.g., Kegel exercises or biofeedback), and a variety of minimally invasive surgical therapies are available as second line therapies. Examples of these second line therapies include sling procedures, bladder neck suspension, transvaginal tape (TVT), etc. In each, the procedure is a day surgery performed on an outpatient basis. Success rates are high, and the procedures have been embraced by the medical community.

In addition, new therapies have been developed to treat stress urinary incontinence, such as the Renessa system offered by Novasys Medical, Inc., which is used in an office-based procedure. U.S. Pat. No. 6,692,490 to Edwards, assigned to Novasys Medical, discloses the treatment of urinary incontinence and other disorders by the application of energy and drugs.

Finally, a majority of males will develop some degree of urinary obstruction from benign prostate hyperplasia (BPH), or "enlarged prostate", over their lifetime. Since urinary obstruction is known to be a cause of overactive bladder, bladder symptoms in males are generally presumed to be secondary to the enlarged prostate. However, resolution of the urinary obstruction (e.g., by one of the many variants of transurethral treatments of the prostate) does not resolve the bladder symptoms in about a quarter of the patients. Thus, it would be desirable to offer a minimally invasive therapeutic procedure targeting these remaining patients whose symptoms remain after prostate therapy.

Further, there is a growing preference for "watchful waiting" for prostate disease, even for cases of actual prostate cancer, and many of these patients will develop symptoms of overactive bladder due to the urinary obstruction from their growing prostate. Thus, there is the potential to provide a therapy that targets the bladder symptoms prior to or instead of providing therapy targeting the prostate itself.

Males also may experience idiopathic OAB, that is OAB not secondary to an enlarged prostate or other urinary obstruction, and require a primary therapy for the OAB symptoms.

In view of the foregoing, it would be desirable to provide a minimally invasive procedure for modulating bladder function to treat or resolve overactive bladder and provides durable relief for patients suffering from these debilitating conditions.

OVERVIEW

The present inventors have recognized, among other things, apparatus and methods configured to provide therapy to non-mucosal target tissue (or a target volume of tissue) to modulate bladder function. In an example, energy can be delivered to denervate selected portions of the bladder, such as afferent nerves located within or proximate to the trigone region of the bladder wall, to modulate bladder function and thereby provide relief for at least one of a sense of urge, incontinence, frequency, nocturia, bladder capacity, or pain.

In some examples, denervation may be accomplished by delivering thermal energy (e.g., using RF energy, microwaves, or high intensity focused ultrasound) to layers of the bladder wall beneath the mucosal layer, such as within or proximate to the trigone region. In the context of this disclosure, tissue of the female anatomy targeted for energy delivery may include one or more tissue layers of the bladder wall beneath the mucosa and extending to (but not including) the anterior vaginal wall, and are collectively referred to herein as "non-superficial tissue." Further, in the context of this disclosure, tissue of the male anatomy targeted for energy delivery may include one or more layers of the bladder wall beneath the mucosa and extending to and including the perivesical fat layer, and in the context also is referred to as "non-superficial tissue". In still other examples, thermal energy may be delivered to neural tissue, such as a pelvic nerve or its branches, within or proximate to the bladder wall to modulate nerve traffic to or from at least a portion of the bladder, thereby modulating bladder function. In accordance with some examples, suction may be used to grasp and conform a mucosal surface of the bladder wall to a first surface of a device, and energy can be delivered to non-superficial target tissue at a substantially uniform depth from the mucosal surface. Cooling also may be provided to reduce heat buildup in the mucosa. However, in some examples, a mucosal surface of the bladder wall superficial to the non-superficial target tissue can be retained substantially intact without cooling, such as by inserting an energy delivery element in the non-superficial target tissue at a substantially uniform distance from the first surface of the device and delivering energy to the non-superficial target tissue from that substantially uniform depth beneath the mucosal surface. The systems and methods described herein may be configured to deliver energy, such as thermal energy, to target tissue either from within a lumen or cavity of a body organ, for example, the bladder, or from a lumen or cavity of an adjacent organ, such as the vagina.

In the alternative, or optionally in addition, the systems and methods described herein may provide that one or more areas of the bladder be isolated or supported such as to suppress the sense of urgency. For example, surgical barriers or treatments may be used to reduce stretch of a selected region of the bladder, such as the trigone, or alternatively used as an adjunct to energy delivery to prevent nerve regrowth in a treated portion of the bladder.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals or letters may describe similar components in different views. Like numerals having different letter suffixes may represent different instances of similar components. The drawings illustrate generally, by way of example, but not by way of limitation, various examples discussed in the present document.

FIGS. 9A and 9B are plan and side section views of the distal region of FIGS. 8A through 8C receiving a portion of bladder tissue, while

DETAILED DESCRIPTION

Figure 1:
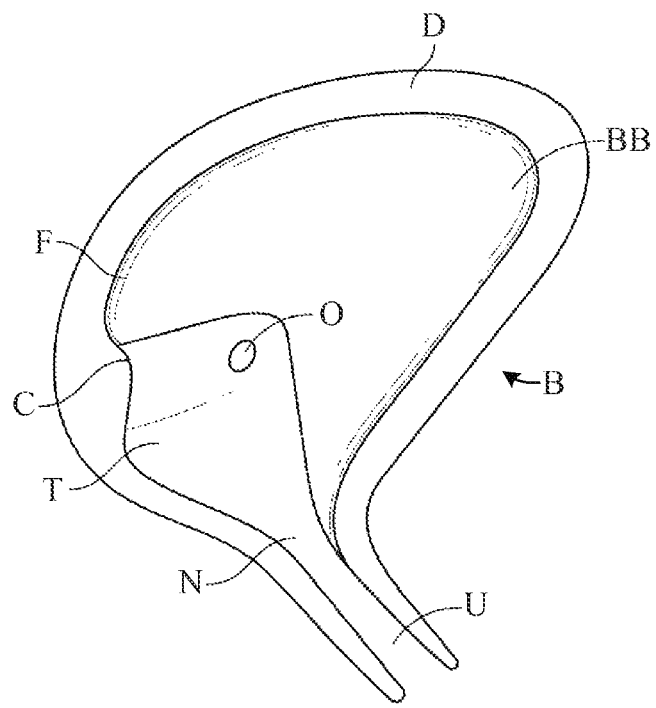
FIGS. 1-3 depict views of anatomical structures to which the apparatus and methods of the present subject matter may be applied to treat overactive bladder.
Figure 2:
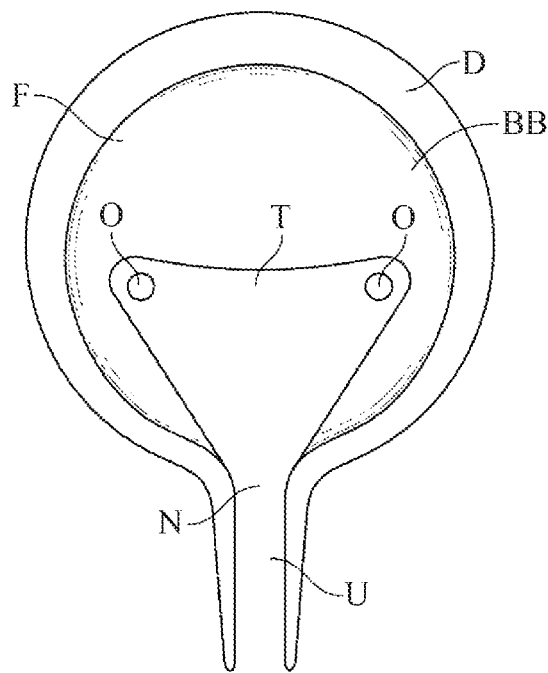
Figure 3:
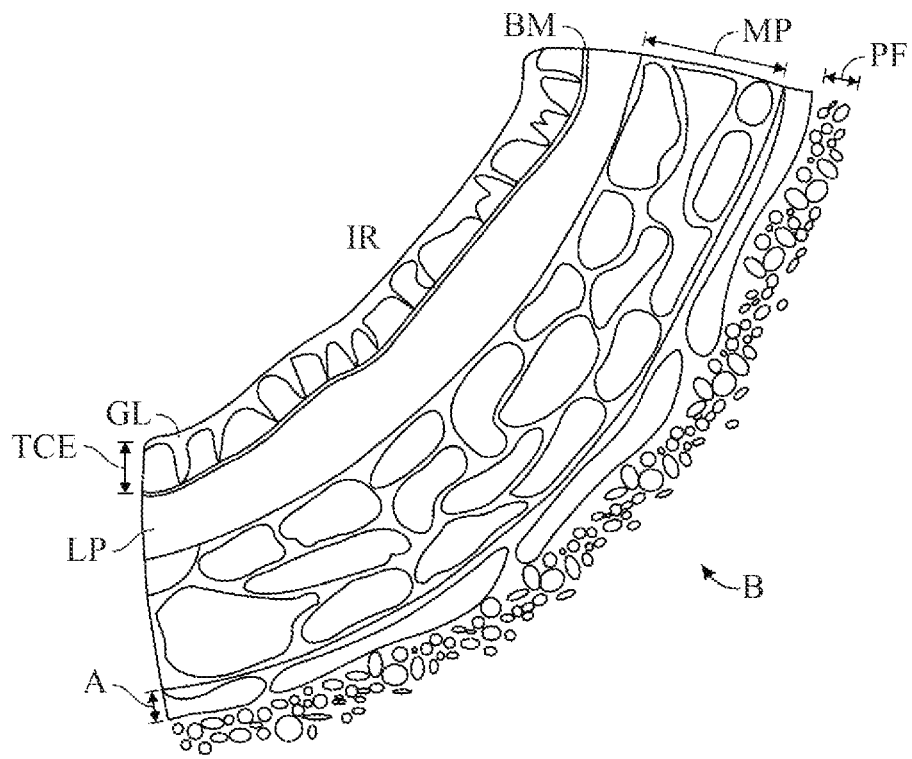

The present inventors have recognized, among other things, apparatus and methods configured to provide denervation of selected tissue within or proximate to a bladder wall at a substantially uniform distance from a mucosal surface of the bladder wall to reduce afferent nerve traffic of the pelvic region from reaching the sacral spinal cord and via ascending spinal cord pathways, the brain. In particular, the apparatus and methods of the present subject matter can be directed to denervating non-superficial tissue, such as non-superficial tissue corresponding to the trigone region of the bladder. By reducing afferent nerve traffic from the pelvic region, subsequent efferent nerve traffic via spinal cord reflexes or subsequent central efferent sympathetic, parasympathetic, or somatic nerve traffic from the brain, will be suppressed. The apparatus and methods described herein may be configured to provide permanent or semi-permanent therapy to modulate bladder function, for example, to improve bladder function relating to urine storage or evacuation, reflux prevention, afferent input to the central nervous system, and phenomena associated with bladder dysfunction, such as incontinence, nocturia, excessive frequency or sensations generated by the bladder, such as urgency, fullness, pressure, pain, etc. Although described throughout this disclosure in the context of female anatomy, it should be understood that the present subject matter also may be advantageously employed in treating pelvic nervous tissue of the male anatomy.

The subject matter disclosed herein can encompass a variety of methods that may be beneficially employed to modulate, ablate, scar, destroy, vaporize, isolate, shrink, stun, paralyze, kill, remove, debulk or disrupt, etc., portions of the non-superficial tissue of the bladder, so as to preserve the mucosal layer, and optionally, deeper bladder tissues (e.g. deep detrusor, adventitial, perivesical fat, etc.) or adjacent organs (e.g., anterior vaginal wall, rectum, etc.). In an example, preserving the mucosal layer or the mucosal surface can include maintaining cellular viability of a substantial portion of either the mucosal layer or the mucosal surface. The apparatus and methods described herein therefore include modalities that mimic or replicate the paralytic or nerve blocking effects of botulinum toxin injections to treat overactive bladder, but provide a more durable and precise procedure—with a shorter onset of action and without the risk of associated systemic and urologic side effects or adverse events.

In one example, the effects of botulinum toxin injections (e.g., 20-30 injections, etc.) into the detrusor muscle or trigone may be replicated by providing energy delivery via electrical (RF) or thermal (high intensity ultrasound, microwave or cryogenically) application of energy to substantially ablate or disrupt afferent nerve traffic in non-superficial tissue of the trigone region of the bladder, while avoiding damage to the inner (mucosal) and optionally, outer layers of the bladder (e.g., deep detrusor, adventitia, perivesical fat or) or adjacent organs (e.g., anterior vaginal wall, rectum, etc.), and without impacting functioning of the urethra, urethral os, ureters, or urethral ostia. Accordingly energy may be applied in a number of patterns, including linear lesions (e.g., crossing or non-crossing), closed loop lesions (e.g., a circle isolating the trigone or portions of the trigone), curved lesions, foot-print lesions, or others are possible.

The foregoing apparatus and methods may be employed not only to treat bladder dysfunction, such as urge incontinency and overactive bladder, but also to reduce symptoms associated with generalized pelvic pain transmitted via the meshwork of afferent nervous tissue located in the trigone of the bladder.

The present subject matter further contemplates the apparatus and methods that may be used alone, or as an adjunct to nerve denervation, to treat bladder dysfunction, such as urgency, frequency, urge incontinence, overactive bladder, nocturia, etc., by stiffening or remodeling the trigone of the bladder. In accordance with this aspect of the present subject matter, mechanical structures may be embedded or formed in situ within the trigone, such as in the non-superficial tissue, that stiffen the trigone region and reduce activation of sense receptors within that region. Such apparatus may include, for example, insertion of biocompatible support bars within the non-superficial tissue of the trigone, injection of drugs or polymers that effect the tissue layer or polymerize in situ to make the tissue layer more rigid, and less susceptible to stretching such as would activate sense receptors to generate nervous traffic corresponding to a sense of bladder fullness. Although described herein as optional, such apparatus and methods can, in certain cases, be used on a stand-alone basis to treat the symptoms of bladder dysfunction. Although denervation of the trigone by energy delivery can provide durable relief of bladder symptoms, mechanical barrier structures implanted adjacent and deep to the denervated region may be used to reduce the likelihood that the nerve meshwork will regenerate by ingrowth from surrounding regions of the bladder.

A. Energy Delivery Modalities

Wide-spread disruption of a mucosa of a trigone of the bladder can result in an increase in overactive bladder (OAB) symptoms (e.g., urgency, frequency, pain, etc.) during the healing phase of the mucosa. For example, when a mucosal layer of the bladder is traumatized (e.g., in the presence of a lesion, such as a Hunner's lesion, in an interstitial cystitis (IC) or painful bladder syndrome (PBS) patient, as the result of fulguration of a small lesion in the bladder, or in the presence or as the result of one or more other traumas), overactive bladder type symptoms can subsist until the mucosal surface can regenerate.

In accordance with one aspect of the present subject matter, non-superficial tissue of the bladder and further tissue extending as far as the anterior vaginal wall, (e.g., corresponding to the trigone region of the bladder) can be treated via energy delivery in amounts sufficient to ablate and denervate nerve pathways disposed within the treated tissue. Preserving the mucosa, or also the external muscular or adventitial layers of the bladder, is effective in preventing fistula or cystocele formation. Energy delivery may be accomplished by any of a variety of modalities, so long as denervation of the non-superficial tissue can be controlled depth-wise to ensure that the treatment does not damage the bladder mucosa or penetrate to a depth that could damage adjacent organs (e.g., the vaginal wall), laterally to ensure that the ureters and ureteral ostia are not damaged, and caudally to ensure that the urethra or the urethral os are not damaged. Energy delivery apparatus of the present subject matter may include systems that induce hyperthermia, such as monopolar or bipolar electrocautery systems, radio frequency (RF), pulsed radiofrequency (PRF), microwave, high intensity ultrasound, contact laser, visual laser, plasma, phase change (e.g., steam to water), hypothermia, such as cryosurgical systems, or mechanical disruptions, such as extracorporeal shockwaves, cavitation or vibration in an amount sufficient to induce tissue necrosis.

In accordance with one aspect of the subject matter, energy may be applied topically (e.g., to an exposed surface, such as exposed by an invasive procedure, to an endoluminal or intravesical surface or to the surface of any other natural body cavity), or by a form configured to penetrate into the tissue layer to be treated (e.g., needle electrode). In accordance with one aspect of the subject matter disclosed herein, tissue treatment can be conducted by delivering the energy directly into the non-superficial tissue to avoid damaging the superficial layers using suction apparatus that draws tissue within an offset region of the apparatus to a precise, predetermined depth. Where topical application of energy is employed, such treatment can be performed while simultaneously or intermittently cooling the mucosal surface, such as described herein below.

Figure 4:
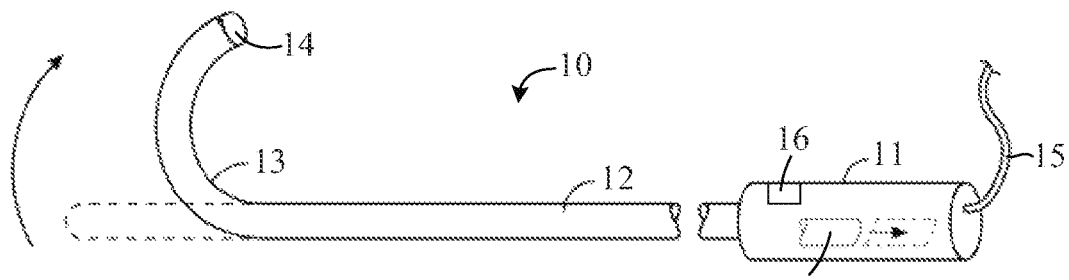
FIG. 4 is a plan view of an exemplary embodiment of a system constructed in accordance with the principles of the present subject matter.

Referring to FIG. 4, exemplary device 10 of the present subject matter is described for delivering energy to the bladder. Device 10 includes handle 11, elongated shaft 12, flexible end region 13 and energy delivery element 14 (or a therapy delivery element). Energy delivery element 14 can be configured to provide therapy to a target volume or to a non-superficial target tissue, and, in certain examples, can include a monopolar or bipolar needle electrode for applying RF energy, a resistive heating element, microwave element, ultrasound or high intensity focused ultrasound, laser, cryotherapy, plasma or phase change or other energy delivery element as are known in the art, so long as the energy delivery element is capable of delivering controlled quantities of energy to specific, targeted, tissue regions. Handle 11 may be coupled via cable 15 to an external power supply (not shown) appropriate for the selected energy delivery element 14. Handle 11 may include button 16 for activating energy delivery via energy delivery element 14, and further include actuator 17 for selectively bending flexible end region 13 from its unflexed position (indicated in dotted line in FIG. 4) to direct energy delivery element 14 into contact with a desired target, for example, under visual guidance provided by a cystoscope. In an example, the elongated shaft 12 can include a length selected to facilitate non-invasive insertion of energy delivery element 14 and flexible end region 13 into the bladder via the urethra. Alternatively, elongated shaft may be configured for passage via a surgical or minimally invasive opening. Device 10 can include durable components suitable for repeated sterilization and reuse with multiple patients, or may be disposable after a single use. In some examples, cable 15 may be omitted, and the external power supply may be incorporated into handle 16.

Figure 5A:
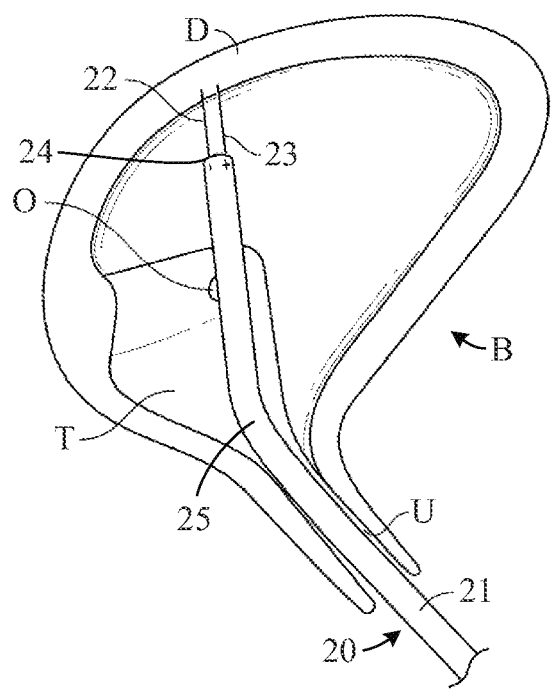
FIGS. 5A and 5B are, respectively, a lateral view of a female bladder within which is inserted the distal region of a device of the present subject matter and a magnified view of the energy delivery element of that device.
Figure 5B:
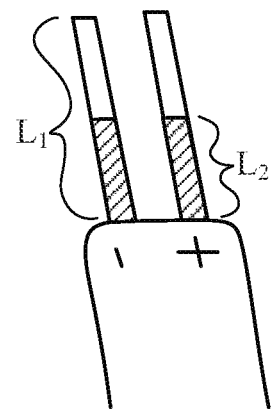

With respect to FIGS. 5A and 5B, is a lateral view of female bladder B showing device 20 having shaft 21 inserted into the bladder with the energy delivery element located between and above ureteral ostium O in contact with the dome of the bladder. Device 20 is similar in construction to device 10 illustrated in FIG. 4, and includes similar components arranged as described for device 10. In this example, the energy delivery element of device 20 includes needle electrodes 22, 23 that extend from distal end 24 of flexible region 25 of elongated shaft 21. In accordance with one aspect of the present subject matter, needle electrodes 22, 23 are configured to extend a total length $L_1$ beyond distal end 24 of flexible region 25 such that the distal ends of the needle electrodes do not extend into the adventitia when fully deployed. In addition, needle electrodes 22, 23 include an electrically insulative coating extending over length $L_2$, such that RF current does not flow between the proximal portions of needle electrodes during energy delivery and thus does not cause hyperthermia in the mucosal layer. In one embodiment, depths $L_1$ and $L_2$ may be approximately 4 to 2 mm, respectively, ensuring that energy delivered by needle electrodes 22, 23 stays predominantly within the non-superficial tissue and avoiding damage to the mucosa and nearby organs and structures.

As will be understood by those of ordinary skill in the art, RF energy delivery has practical advantages of being relatively inexpensive, with low cost generators readily commercially available. In addition, materials used to manufacture RF electrodes are relatively low cost and suitable for disposable devices. RF electrodes also tend to generate the most intense energy density, and therefore heat, immediately near the electrode tips, with energy density falling off quickly with distance. Accordingly, needle electrodes 22, 23 may be used to ablate a readily definable zone within a tissue. Alternatively, RF may be used to deliver energy at lower levels to generate temperatures appropriate to remodel collagen located within the targeted tissue, without causing necrosis. At lower power densities and with careful control to limit tissue temperatures, heat may be used to denature collagen without frank ablation. Denatured collagen will tend to shrink, thicken, and stiffen, although strength is initially diminished until healing takes place.

Bi-polar radio frequency (RF) needle ablation is particularly useful for targeted ablation, as bi-polar RF needle electrodes may be used to achieve highly localized ablation in the region between the needles, with little or no current spreading elsewhere in the body. Bi-polar RF needle ablation can also obviate the need for a separate grounding plate and risks from inadequately placed or missing grounding plates, such as skin burns, etc. In an example, the target area can include a target volume of tissue between and along at least a portion of the needles.

Using a bipolar configuration, with substantially parallel RF ablation needles, an ablation region shaped like a figure-eight in cross section can be created in a target tissue. In particular, narrow needle placements (e.g., 3 to 5 mm distance between the needles), can be employed with conventional electrosurgical generators to yield thin (e.g., less than 5 mm) ablation zones, thereby protecting both the superficial mucosal layer and deeper layers beyond the desired ablation zone. In an example, needle spacing on the order of 3 to 5 mm and needle depths on the order of 3 to 5 mm can result in ablation regions that can protect both the superficial mucosal layer, such as the mucosal surface, and in certain examples, deeper layers beyond the desired ablation zone.

Figure 6:
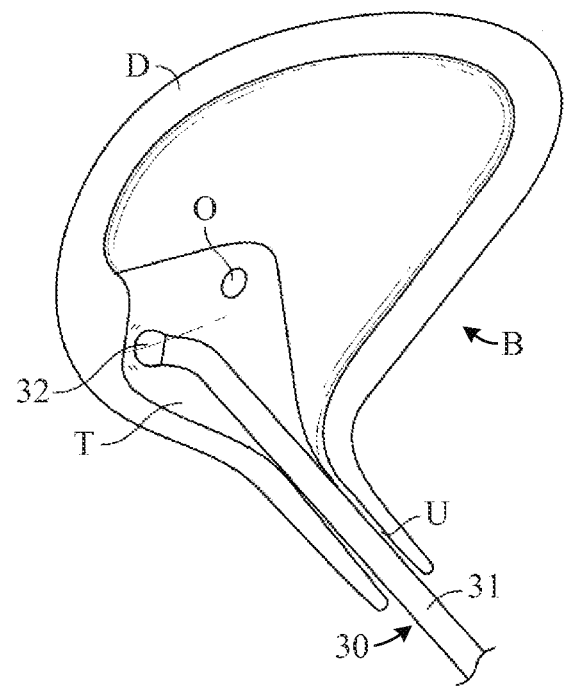
FIG. 6 is a lateral view of a female bladder within which is inserted the distal region of an alternative embodiment of a device of the present subject matter.

FIG. 6 is a lateral view depicting device 30 having shaft 31 inserted into a female bladder (B) with the energy delivery element disposed in contact with trigone (T) of the bladder in an area between and below ureteral ostium (O). Device 30 is similar in construction to device 10 illustrated in FIG. 4, and includes similar components arranged as described for device 10. In this embodiment, energy delivery element 32 can include a microwave or high intensity focused ultrasound elements, which are known in the art as being capable of causing ablation at a specified tissue depth without causing necrosis of intervening tissue. Energy delivery element 32 is disposed on flexible end region 33, which may be articulated or bent using actuator located on the handle of device 30 to cause energy delivery element 32 to contact the tissue surface substantially perpendicularly, as may be confirmed visually using a cystoscope. In this manner, the physician can confirm that energy delivery from energy delivery element 32 is normal to the tissue surface, and thus will denervate or ablate the desired tissue layers without damaging intervening tissue layers. Microwave technology as may be employed in device 30 is moderately more expensive and complex than the RF technology employed in device 20 of FIGS. 5A and 5B, with a higher cost of disposables associated with manufacture of the microwave antenna. However, as noted above, microwave offers the advantage of being able to design a "field" effect, with more uniform energy density and greater depth of penetration than for RF. While in FIG. 6 the device 30 is depicted in contact with the trigone, in other examples, the device 30 can be configured target other locations within the bladder, such as detrusor muscle (D), etc.

It should be understood that other energy delivery modalities may be beneficially employed in apparatus constructed in accordance with the principles of the present subject matter, including RF energy, low frequency AC energy, DC pulse energy, plasma, etc., to cause tissue necrosis and denervation, provided that such energy modalities be configured to provide energy at selected depths and with sufficient precision to avoid damage to the ureters, ureteral ostia, urethra, and urethral os. For example, laser technology, of any wavelength, is relatively expensive due to the cost of the laser itself. However, laser technology has the advantage of being able to choose a specific wavelength of light that offers the optimal penetration and absorption characteristics for the desired therapy. Laser therapy can include interstitial laser coagulation (ILC), laser interstitial thermal therapy (LITT), laser-induced interstitial thermotherapy, laser-induced thermotherapy, interstitial laser therapy, or the like.

A variant of laser therapy is photodynamic therapy, where a photosensitizer is used in combination with a light source (e.g., laser, etc.). The combination of the photosensitizer, light, and tissue oxygen leads to the destruction of tissue exposed to the light. The photosensitizer can be delivered systemically via intravenous therapy (IV), but can also be delivered intravesically, such as to reduce or eliminate systemic effects (e.g., several weeks of sunlight sensitivity, etc.). Energy delivery may also be accomplished via other modalities, including heat therapy, such as using hot water balloons, free-flowing hot water, steam, etc. or cryotherapy, which may be used to freeze selected tissues, as described in later examples.

B. Tissue Suction-Enabled Embodiments

Figure 7:
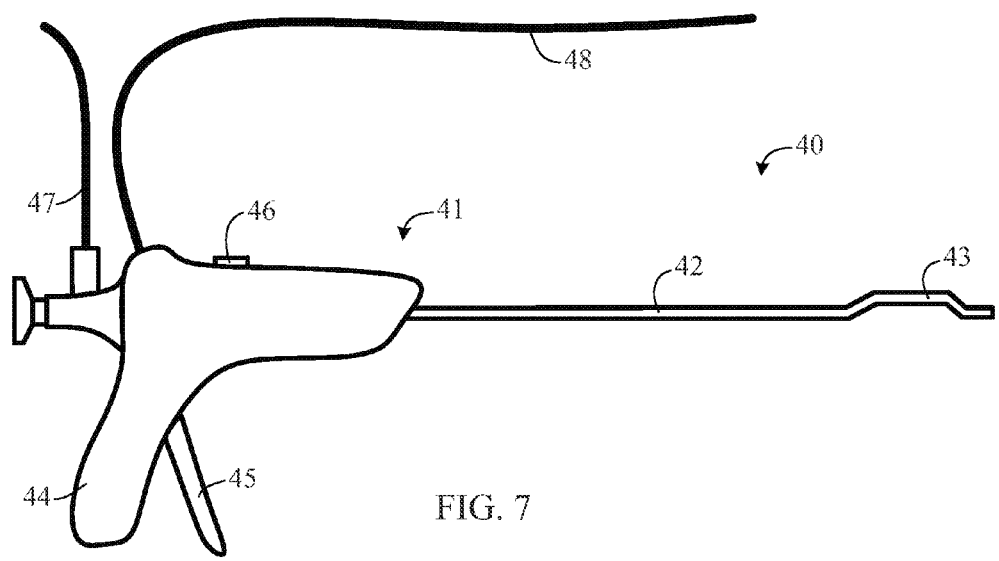
FIG. 7 is a plan view of a further alternative embodiment of a device of the present subject matter that employs suction to grasp and conform a target tissue.

Referring now to FIGS. 7 through 9, an exemplary embodiment of the present subject matter is described in which a device including an elongated shaft having a distal region is configured to receive a tissue surface (e.g., a mucosal surface of a bladder wall), superficial to a target volume, at a first surface of the distal region. A therapy delivery element having a longitudinal portion (e.g., one or more needles, etc.) can be configured to be inserted or disposed in a target volume at a substantially uniform distance from the first surface to provide therapy to the target volume. In an example, suction or one or more other forces can be employed to bring the tissue surface in contact with the first surface (e.g., to grasp and conform, etc.), so that, when the therapy delivery element is disposed in the target volume, ablation or other therapy can be obtained at a predetermined depth below the mucosal surface of the bladder. In certain examples, ablation or other therapy can be obtained in the target volume while retaining a mucosal surface of the bladder wall superficial to the target tissue substantially intact. In an example, retaining the mucosal surface substantially intact can include not heating the tissue to a sufficient level to cause ablation or shrinkage of the mucosal surface. In another example, the retaining the mucosal surface substantially intact can include maintaining cellular viability of the mucosal surface (e.g., protecting or not killing the cells of the mucosal surface), or preserving the glycosaminoglycan layer (e.g., by avoiding denuding of the glycosaminoglycan layer).

In FIG. 7, device 40 includes handle 41 coupled to elongated shaft 42 and distal region 43. Handle 41 has pistol grip 44 that includes actuator 45, button 46, is coupled to cable 47 and suction line 48. When depressed, actuator 45 can cause needle electrodes housed within elongated shaft 42 to extend from the proximal end to the distal end of distal region 43, as described in greater detail below. Button 46 activates the application of RF energy to device 40. Cable 47 is coupleable to an RF electrosurgical generator of conventional design. Suction line 48 is coupleable to conventional source of vacuum, which may include either a commercial suction pump or suitably controlled "house" vacuum available in the hospital setting or physician's office. Optionally, handle 41 may include an eye piece for optically examining the positioning of distal region 43, or alternatively may include a video imaging module and suitable electronics for generating a video image that may be displayed on a conventional television or computer monitor. Alternatively, handle 41 may be configured to be attached to an auxiliary rigid or flexible cystoscope, as are per se known.

Figure 8A:
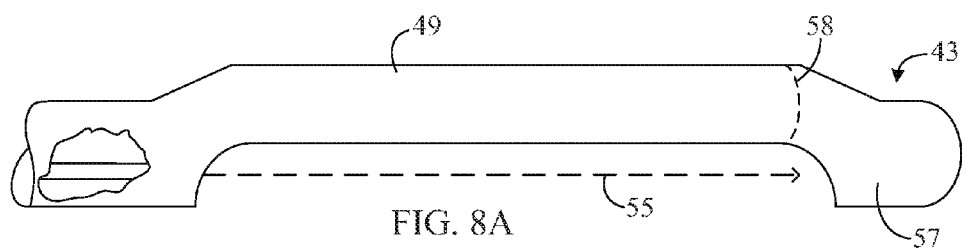
FIGS. 8A to 8C are plan, bottom and sectional views, respectively of the distal region of the device of FIG. 7.
Figure 8B:
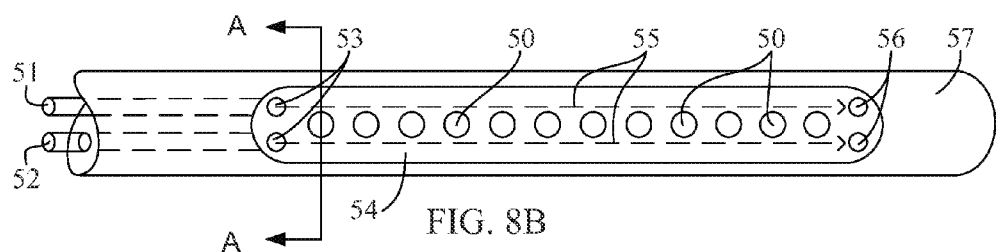
Figure 8C:
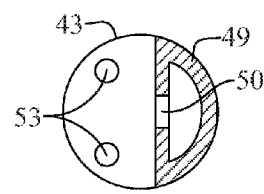

FIGS. 8A and 8B depict plan and bottom views of distal region 43 of FIG. 7, while FIG. 8C depicts a sectional view of distal region 43 taken along the view line A-A in FIG. 8B. As shown in FIG. 8A, distal region 43 includes offset portion 49 that functions as a manifold through which suction is drawn through plurality of apertures 50. Bipolar needle electrodes 51, 52 are disposed in channels 53 of elongated shaft 42 and coupled to actuator 45 (see FIG. 7) via a suitable linkage. When actuator 45 of handle 41 is depressed, needle electrodes 51, 52 extend across offset region 54 of distal region 43 (as indicated by dotted lines 55 in FIGS. 8A and 8B. Optionally, distal-most portion 57 of distal region 43 may include channels 56 that capture the distal ends of needle electrodes 51, 52 when the needles are extended fully across offset region 54. Alternatively, distal-most region 57 and channels 56 may be entirely omitted, such that offset portion 49 terminates at dotted line 58 depicted in FIG. 8A.

In the embodiment depicted in FIGS. 8A and 8B, needle electrodes 51, 52 are relatively long (e.g., 15 to 20 mm) and oriented parallel to one another to provide a uniform depth, generally planar ablation zone. So as to provide an ablation zone at a uniform depth in the tissue, needle electrodes 51, 52 are disposed in a plane separated from offset portion 49 of distal region 43 having a predetermined distance. As will be apparent to one of ordinary skill in the art, the distance between the inserted needle electrodes and the first surface of offset portion 49 configured to receive the mucosal surface may be selected to provide an ablation zone at a desired depth in or from the bladder wall. In addition, a plurality of sizes of offset portion 49 may be constructed so that a device suitable for the anatomy of a particular patient may be selected. Accordingly, when tissue (e.g., bladder trigone tissue) is received or grasped in offset region 54 against the first surface of offset portion 49 of distal region 43, advancement of the needle electrodes 51, 52 results in extension of the needle electrodes into the tissue at a depth that is equivalent to the distance between the first surface of offset portion 49 and the inserted needle electrodes.

While the embodiment of FIGS. 8A and 8B employs straight needles and a geometrically flat first surface of offset portion 49, other configurations may be readily constructed. For example, the needle electrodes may include a defined radius or curvature, for example, in conjunction with a first surface of offset portion 49 having a defined radius or curvature (e.g., the curvature of the needles). In such an embodiment, the depth of delivery of the needle electrodes may be defined by the difference in radii of curvature.

In an example, the needles can be configured to be inserted into and disposed in a target volume of tissue at a substantially uniform distance from the first surface of the offset portion. In an example, when fully inserted, the length of the needles can approach or exceed 15 mm. In certain examples, over the span of 15 mm, the substantially uniform distance between the needle and the first surface of the offset portion can range from 0 to 6 mm, with the lower range associated with a tighter zone of ablation. If the substantially uniform distance is too great, the layered ablation becomes harder to control. In an example, the range can include 0 to 3 mm, 0 to 2 mm, and 0 to 1 mm, etc.

Other means for ensuring good tissue approximation within offset region 54 may be readily envisioned. The bladder trigone and its underlying tissues, such as the anterior vaginal wall in the case of the female patient, are quite mobile and easily deformed. Thus, only modest forces can be required to urge the bladder trigone to conform to the offset region of the device. For example, a counter-pressure from the opposite side can be used to cause the distal end of the bladder device to receive the tissue at a first surface, in certain examples, conforming the tissue to the distal end of the bladder device. In the female patient, the counter-pressure may be applied from the vagina; in the male patient, the counter-pressure may be applied from the rectum. Such counter-pressure may be provided by the fingers of a physician or may be applied using a rigid or semi-rigid probe as illustrated for later examples. In addition, the profile of the probe may be configured to mate with the profile of the bladder device. In this manner, the two mating profiles may be used to clamp the bladder and associated tissue (and either vaginal or rectal tissue, depending on the sex of the patient) therebetween. The probe and the bladder device also may include orienting features or linking mechanisms to enable simple and repeatable clamping of the tissue, such as magnets (e.g., of opposite polarity, inserted into an opposing body cavity, such as the rectum, the vagina, etc.).

In the examples of FIGS. 8A and 8B, suction can be used to firmly, yet reversibly conform the tissue to offset region 54 of distal region 43, by atraumatically grasping and holding the tissue to the distal region 43. Apertures 50 are connected, such as using sealed channels or tubing, to an external vacuum pump that supplies the suction. A variety of configurations, such as holes, slots, meshes, etc., may be used to provide conforming pressure. The apertures may be connected using substantially leak-tight channels located within or proximate to the shaft of the device to an external vacuum pump. Suction fixation of tissue to device 40 is simple, quick, and easily maintained while passing the needle electrodes into the tissue. Needle electrodes 51, 52 may be, for example, 22 gauge needles (or other gauge needles) that pass easily through the tissue, tracking along a straight line and exiting the tissue in the same geometric plane as they entered the tissue. The use of suction beneficially distributes the holding force over a large surface area without causing harm to the tissue.

The design of the embodiment of FIGS. 8A and 8B further lends itself to the inclusion of a number of safety features. First, direct vision capability may be used to locate or position device 40. For example, a channel may be incorporated into the shaft of device 40 that allows insertion of a traditional urethroscope or other visual device for visual confirmation of the location or placement of the active portion (e.g., suction zone, needle electrodes, etc.) of device 40. Second, the order of operation (e.g., initiation of suction, capture of tissue, needle electrode advancement, RF power application, needle electrode retraction, release of tissue, termination of suction, etc.) of device 40 may include a variety of safety interlocks, mechanical/hardware or software, to ensure the correct order of operations. For example, one or more of the following features may be incorporated to ensure safe operation of device 40:

needle electrode advancement may be prevented until a pressure gauge records that tissue has been firmly captured within offset region 54 by suction through apertures 50;

power to the needle electrodes may be prevented until the needle electrodes are extended;

complete and correct needle electrode advancement may be confirmed by electric or mechanical contacts, and RF power prevented until this confirmation; and suction may be applied until needle electrodes are retracted.

The needle electrodes also may be automatically retracted (e.g., by a spring that has been stretched as they were inserted, by an electromechanical actuator, etc.) if suction tissue capture was lost (e.g., as registered by a pressure gauge). Device 40 can include secondary mechanism (e.g., a failsafe mechanism) for retracting the needle electrodes if the device or mechanism otherwise jams or fails to perform as intended.

Figure 9A:
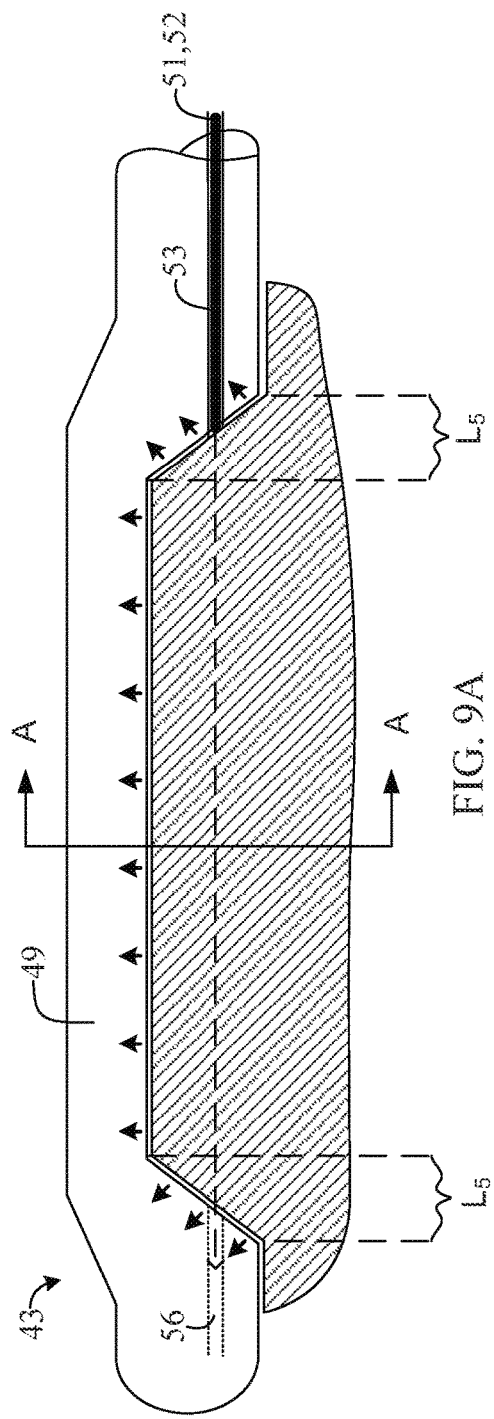
Figure 9C:
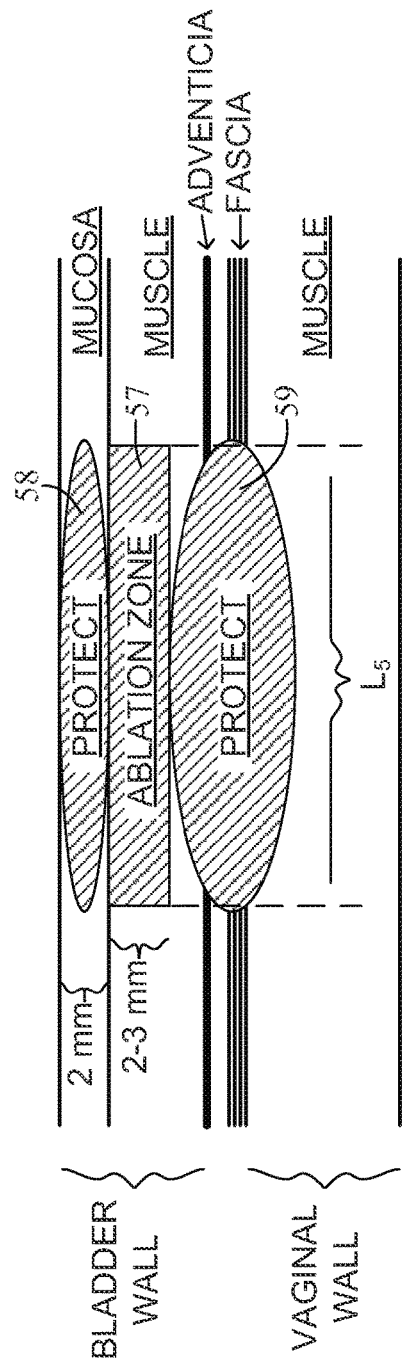
FIG. 9C is schematic diagram illustrating the ablation zone formed by the device of FIGS. 7 9.
Figure 9B:
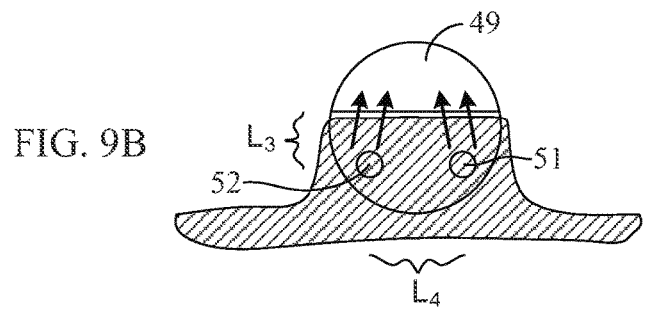

As illustrated schematically in FIGS. 9A and 9B, when distal region 43 is disposed in contact with tissue, for example trigone, and suction is coupled to device 40 via suction line 48, a portion of the tissue is drawn into offset region 54, such as using one or more suction ports (e.g., denoted by the arrows in FIGS. 9A and 9B) to a depth $L_3$. Depressing actuator 45 can cause needles 51, 52 to penetrate and extend across the portion of the tissue captured in offset region 54 until the distal ends of the needles engage channels 56 disposed in the distal-most portion for distal region 43. In an example, having needle electrodes engage channels 56 locks device 40 on to the tissue during the ablation process. Actuation of button 46 on handle 41 causes RF current to flow between needle electrodes 51, 52, thereby causing uniform ablation of tissue captured between the needles.

In accordance with one aspect of the present subject matter, depth $L_3$ is selected to so that only tissue located wherein a predetermined non-superficial layer is ablated during energy delivery. The width of the ablation zone is determined by the energy delivered into the tissue, as well as the spacing $L_4$ (see FIG. 9B). Optionally, needle electrodes 51, 52 may include an electrically insulative coating disposed over a length $L_5$ of the needle electrodes where they exit channels 53 and enter channels 56 (when fully extended across offset region 54), to reduce energy deposition into the mucosa where the needle electrodes penetrate the tissue. Illustratively, offset region 54 in distal region 43 has a length of about 15 to 20 mm, depth $L_3$ can be about 4 mm, and width $L_4$ between the needles is about 1 to 7 mm.

As illustrated in FIG. 9C, the configuration of device 40 ensures that a highly repeatable and well-defined ablation zone 57 of length $L_6$ that is created at a predetermined depth in the non-superficial layer, while also providing protection zones 58, 59 that mitigate damage to mucosal layers and tissue regions outside of the bladder, such as the vaginal wall. In certain examples, offset region 54 of $L_4$ is selected to create ablation zone 57 having a depth of about 2 to 3 mm. It should be understood, however, that the width and depth of the ablation zone may be tailored to a specific patient's anatomy by adjusting the energy delivery parameters. For example, the bladder thickness for a patient may be determined using ultrasound imaging, and the RF energy parameters adjusted accordingly based on the observed thickness (e.g., using a look-up table available in the instruction manual accompanying device 40). In addition, device 40 may be manufactured in a number of sizes, each having a different offset region 49 that provides a specified length and depth L for offset region 54 of distal region 43, and width $L_4$ between the needle electrodes.

Figure 10A:
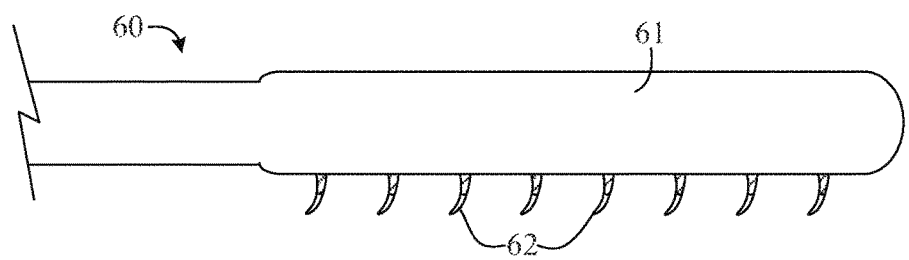
FIGS. 10A and 10B are, respectively, a plan view of the distal region of an alternative embodiment of the device of FIG. 7 that employs retractable needle electrodes, and a magnified view of a portion of such needle electrodes.
Figure 10B:
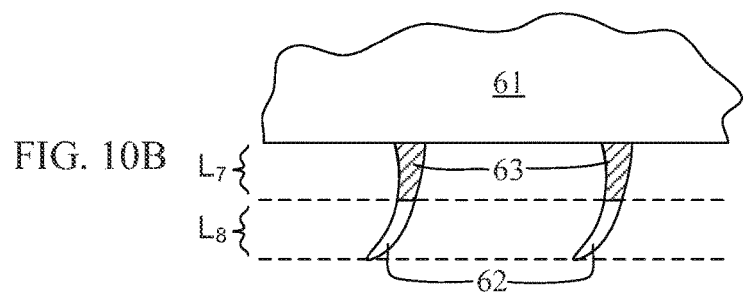

Referring now to FIGS. 10A and 10B, the distal region of an alternative embodiment of a bipolar RF, suction-enabled device 60 of the present subject matter is described. Device 60 is similar in construction to that depicted in FIG. 7, except that device 60 includes a differently configured distal region 61. In particular, instead of a single pair of needle electrodes that are deployed axially as described for the preceding embodiment, device 60 includes a plurality of needle electrodes 62 that are selectively extended from distal region 61 by depressing the actuator on the device handle. As shown in FIG. 10B, needle electrodes 62 can include an electrically insulative coating 63 that extends over a proximal length $L_7$ of the electrodes, to reduce energy delivery into the mucosal layer. Like device 20 depicted in FIGS. 5A and 5B, needle electrodes 62 extend a maximum distance La when fully deployed that ensures that the tips of needle electrodes do not extend into or through the adventitia. Illustratively, depths $L_7$ and La are about 2 mm and 4 to 5 mm, respectively.

Figure 11A:
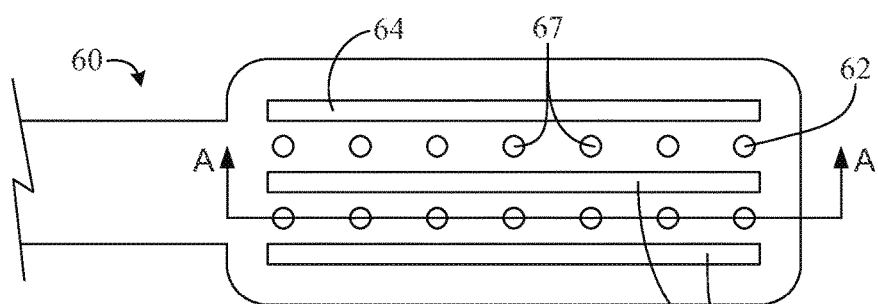
FIGS. 11A and 11B are, respectively, bottom and side sectional views of the distal region of the device of FIGS. 10A and 10B.
Figure 11B:
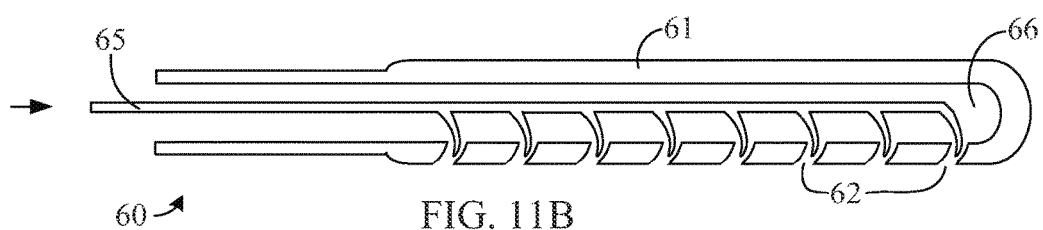

Referring to FIGS. 11A and 11B, distal region 61 includes plurality of slots 64 through which suction is drawn to secure distal region 61 to tissue to be treated. As depicted by the sectional view of FIG. 11B, needle electrodes 62 are joined to member 65, which positioned in suction manifold 66 and is configured to be advanced and retracted by operation of the actuator on the handle of the device, thereby selectively extending or retracting plurality of needle electrodes 62 through apertures 67.

Figure 12:
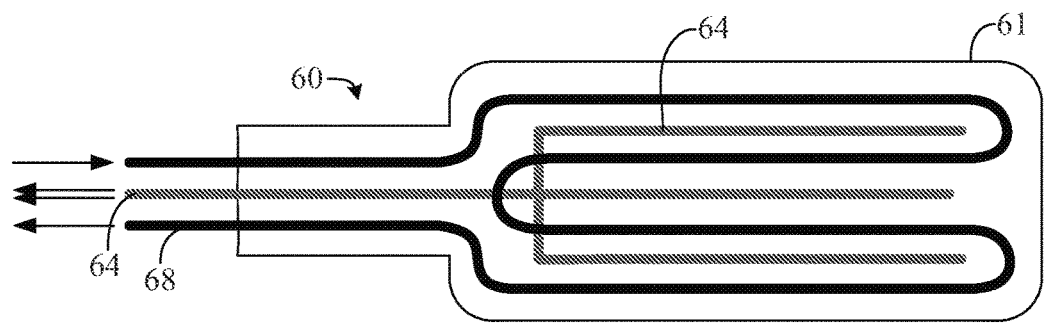
FIG. 12 is a sectional view of an alternative embodiment of the device of FIGS. 10 and 11 showing an optional cooling channel configuration.

FIG. 12 depicts a further alternative of device 60 of FIGS. 10 and 11, in which distal region 61 includes a heat sink for cooling the superficial layers of bladder tissue during operation of needle electrodes 62, including a cooling channel 68 disposed in a separate plane of distal region 61 above slots 64 through which suction can be drawn. In this manner, a coolant, such as chilled saline, may be circulated through coolant channel 68 during the ablation procedure to act as a heat sink that draws heat away from the mucosal layer, and reduces the risk of superficial damage. Alternatively, the heat sink for cooling can include separate channels in distal region 61 that permit a chilled biocompatible fluid, such as chilled saline, to be infused between distal region 61 and the bladder surface to reduce excess heat buildup that could damage the mucosa.

As will be apparent from the preceding description, device 60 is used to cause ablation zones of predetermined size within the non-superficial tissue of the bladder. In operation, distal region 61 of device 60 is inserted into the bladder (e.g., through the urethra or a minimally invasive opening through the bladder wall), such that distal region 61 is disposed in contact with tissue, for example, the trigone. Then, suction is coupled to device 60 via a suction line so that suction is drawn through slots 64 and apertures 67, thereby engaging distal region 61 into contact with the tissue. While suction continues to retain the tissue in contact with distal region 61, the actuator on device 60 is depressed to advance member 65 and fully extend needles 62 to penetrate the bladder wall. RF energy is then supplied to needles, which causes RF current to flow between needle electrodes 62 (or between needle electrodes and a grounding pad if a monopolar configuration is used), thereby causing a substantially uniform ablation zone for tissue received at the distal region 61. As discussed above, insulative coating 63 can ensure that the delivered energy does not damage the mucosa, while the overall deployed length of needle electrodes 62 can ensure that ablation does not penetrate to the anterior vaginal wall, and is confined within the bladder wall.

C. Exemplary Methods

Figure 13:
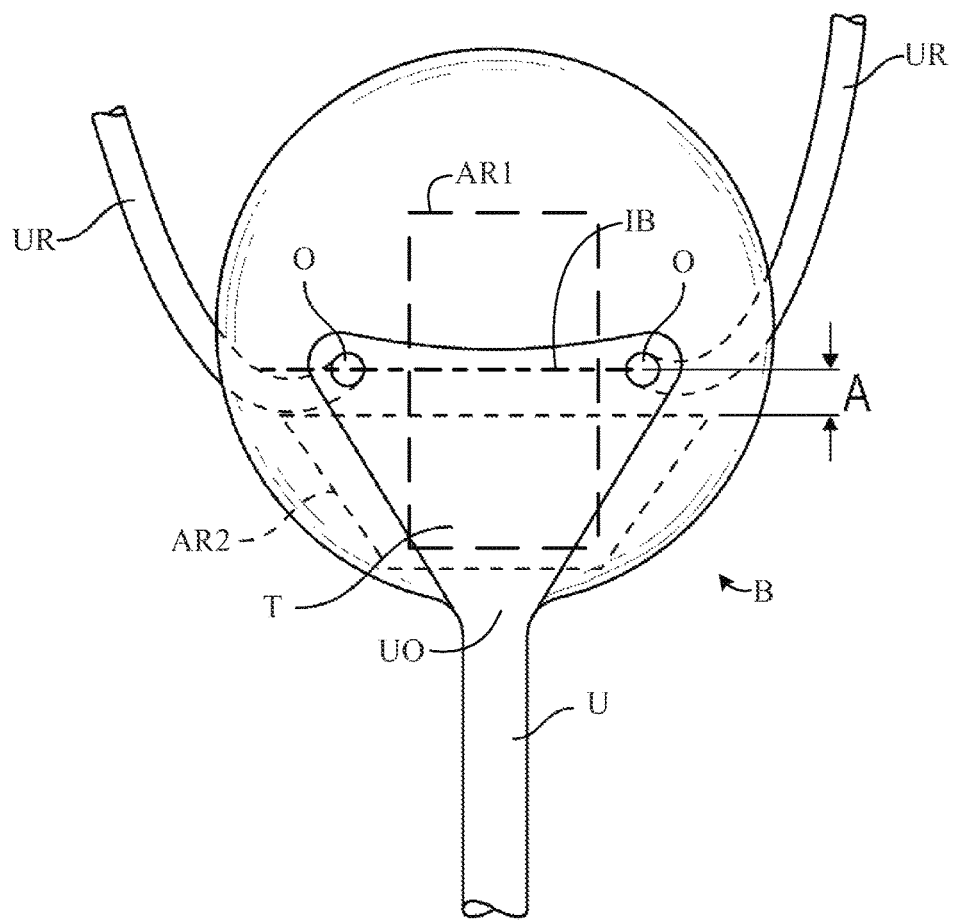
FIG. 13 is an interior view of the posterior of a female bladder showing associated vessels, the location of the trigone, and alternative possible ablation regions.

With respect to FIG. 13, illustrative methods of treating bladder dysfunction in accordance with the present subject matter are described. FIG. 13 is an exemplary interior view of a female bladder (B) looking toward a posterior trigone (T), and further illustrating the relative locations of ureteral ostia (O), ureters (UR), urethral os (UO), and urethra (U), and a dashed line extending between the ureteral ostia representing an imaginary interureteric bar (IB). The distance between ureteral ostia may vary between approximately 2 to 5 cm, depending upon body size and the volume of fluid in bladder. The distance between urethra and interureteric bar is approximately 3 cm, depending upon body size and the volume of fluid in the bladder. Area proximate or including the ureters, ureteral ostia, urethral os, or urethra should be avoided during therapy, so as to avoid inadvertent damage to these structures, and thus maintain normal function of the urethra, urethral os, ureters, or ureteral ostia.

FIG. 13 further depicts examples of different ablation regions AR1, AR2, constituting regions of the bladder in which it may be desirable to ablate or denervate all or substantially all of the non-superficial tissue in those regions. Ablation region AR1 illustratively is located at least one of below (e.g., caudal to) or between ureteral ostia, and may approach ureteral ostia, but leaving a safety region between ureteral ostia and ablation region AR1 of at least one of 1 to 25 mm, 1 to 20 mm, 2 to 10 mm, or 2.5 to 7.5 mm. For example, an upper border of ablation region AR1 may extend above interureteric bar, towards the dome of the bladder by at least one of 0 to 30 mm, 0 to 20 mm, or 0 to 10 mm. In other cases, the upper border of ablation region AR1 may extend below interureteric bar towards the base of the bladder by at least one of 0 to 20 mm or 0 to 10 mm. The lower border of ablation region AR1 may extend above urethra or the neck of the bladder by at least one of 2 to 25 mm, 2 to 20 mm, 2 to 10 mm, or 2 to 5 mm, so as to avoid inadvertent damage to urethra or the internal urethral sphincter.

At least a portion of ablation region AR1 may be beneficially targeted for therapy. The bladder may be emptied prior to the ablation procedure to provide for a thicker wall (e.g., a mucosa plus muscle layer thickness between 8 to 15 mm), or filled prior to the ablation procedure to provide for a thinner wall (e.g., a mucosa plus muscle layer thickness between 2 to 5 mm), or partially filled to provide a thickness between that of an empty and full bladder (e.g., mucosa plus muscle layer thickness between 3 to 14 mm). The selected depth of penetration of the therapy from an inner wall of the bladder may be between at least one of 0 to 3 mm, 0.5 to 5 mm, or 5 to 15 mm.

Still referring to FIG. 13, alternative exemplary ablation region AR2 is substantially trapezoidal in shape and roughly approximates the shape of trigone. In this case, ablation region AR2 approaches ureteral ostia, but again leaving a safety region between ureteral ostia and the outer margin of ablation region AR1 of at least one of 1 to 25 mm, 1 to 20 mm, 2 to 10 mm, or 2.5 to 7.5 mm. Although ablation region AR2 illustratively is substantially trapezoidal, other shapes or sizes may be used, such as substantially rectangular, triangular, arcuate, ovoid, etc. A single portion of ablation region AR2 may be targeted by providing energy delivery to create one or more lesions. In an example, multiple portions of ablation region AR2 may be treated, within a single treatment or multiple treatments. Treated portions of an ablation region may overlap, as described below.

It should be understood that each of ablation regions AR1, AR2 should be selected so as avoid damage to the ureters, ureteral ostia, urethra and urethral os. In addition, precautions may be taken to ensure that such damage does not occur accidentally. For example, one or both of the ureters may be cannulated using a guidewire, a pigtail, a catheter or a balloon nipple, and optionally a water filled balloon, to reduce transfer of energy to the ureters or ureteral ostia. Alternatively or in addition, a device may be used to aid in observation or confirmation of the location of the ureteral ostia during therapy. Such a device may include a visualization device configured to provide a visual confirmation of the location of the ureteral ostia, such as a cystoscope. Alternatively, a device configured to cannulate and provide access to the ureteral ostia, a device configured to provide one or more markers or "flags" to increase the visibility of the ureteral ostia, a device configured to be inserted into the ureteral ostia to shield or protect the ureteral ostia from exposure to energy (e.g., a plug, a cover with a circumference larger than the circumference of the ureteral ostia 102), may be employed. Alternatively, a device configured to be inserted into a ureteral os that ablates a known distance from the uretal os (e.g. 2 mm or more from the uretal os) may be employed.

For example, device 40 of FIG. 7 may include a guide wire lumen disposed on upper surface of distal region that accepts a conventional guide wire in an over-the-wire or rapid exchange manner. In use, a distal end of a guide wire can first be inserted through a ureteral os and extended a distance into the ureter, for example, under visual guidance of a cystoscope. Distal region 43 of device 40 then may be back loaded on the proximal end of the guide wire through the guide wire lumen, and distal end 43 of the device 40 is advanced along the guide wire through the urethra and into the bladder. When device 40 is fully inserted into the bladder, offset portion 49 of device 40 (see, e.g., FIG. 8A) will cause offset region 54 of device 40 to receive the bladder wall near the ureteral os at a distance no closer than the thickness of offset portion 49 of the device. This distance accordingly may be selected during design of offset portion 49 of device 40 to provide a desired margin of tissue between the ureteral ostia and the ablation zone, thereby facilitating placement of the device during use and ensuring that the ablation zone does not encompass sensitive areas, such as the ureters and ureteral ostia.

Additionally, because the distance between the ureteral ostia varies depending upon body size or the volume of fluid in the bladder, a measuring device, coupled to a visualization device, the treatment device, or other device configured to be inserted into the bladder, may be used to measure the distance between the ureteral ostia. As a further example, a measuring device may include an expandable member, such as a balloon, having calibration marks that may be compared to the distance between the ureteral ostia. In this case, the treatment device may be selected or adjusted in response to the measured distance or the volume of the bladder may be adjusted, such as by introducing or removing fluid to provide a desired distance between the ureteral ostia.

Figure 14:
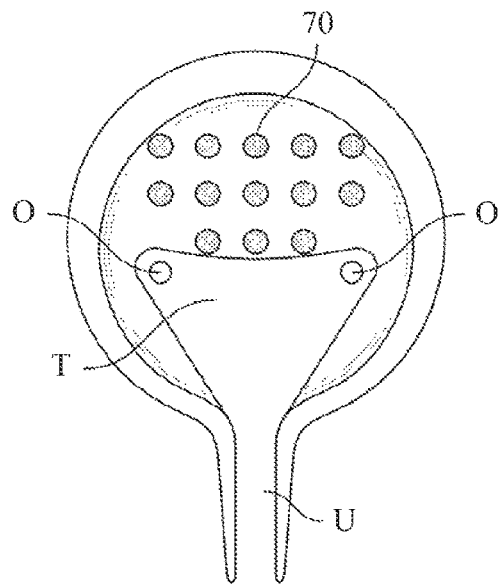
FIGS. 14-17 are interior views of the posterior of a female bladder showing various ablation patterns.

Referring now to FIGS. 14 through 17, illustrative ablation patterns that may be generated within bladder B are described. Each of FIGS. 14 through 17 illustrates a posterior view of a view of the interior of bladder (B), with ureteral ostia (O), trigone (T), and urethra (U) identified. More specifically, FIG. 14 depicts a pointillist ablation pattern such as may be created using the single contact point devices of FIGS. 4-6. FIG. 14 depicts the contact area of the energy delivery element as shaded circles 70, with the concentric dotted lines illustratively indicating the ablation zone corresponding to each contact area. As will be observed in FIG. 14, most of the dotted concentric circles overlap, including a substantially total ablation of the non-superficial tissue in the targeted treatment area. Illustratively, an expanded or reduced subset of target areas similar to those used for botulinum toxin injections may be employed to define the treatment area.

Figure 15:
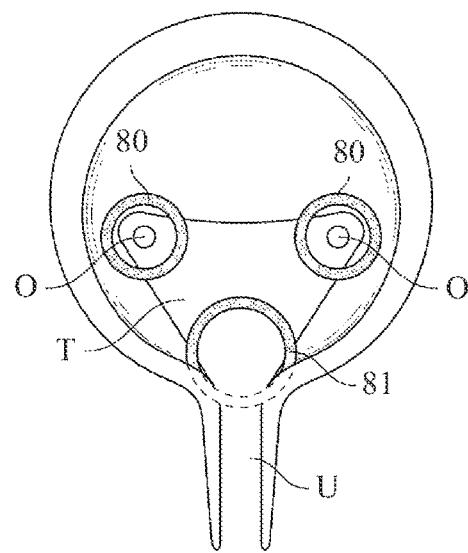
Figure 16:
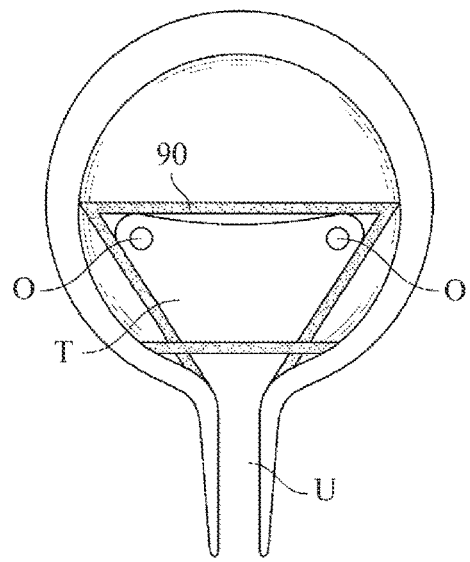

FIG. 15 depicts a generally circular ablation pattern targeting the edges of trigone (T), by ablating substantially circular ablation patterns 80 and 81 around ureteral ostia (O) and ablation arc 81 located about the urethral ostium. The circular patterns depicted in FIG. 15 may be generated using, for example, energy delivery elements as described above, such as microwave, high intensity ultrasound, laser, etc. Such devices may likewise be used to create ablation pattern 90 depicted in FIG. 16, which substantially circumscribes trigone. Other ablation patterns also may be used, such as non-crossing or crossing linear ablation patterns, concentric ablation patterns that target an atypical region of the bladder wall. For example, an atypical region of the bladder may include one or more areas of unusual morphology or activity, such as areas of denervation or increased local contractile activity or electrical foci. In such cases, targeting therapy at the atypical regions of the bladder may provide advantages similar to those provided by electrophysiology treatments in the heart, such as ablation or isolation of an ectopic focus or ectopic foci for cardiac arrhythmias (e.g., to treat atrial fibrillation, tachycardia, etc.).

Figure 17:
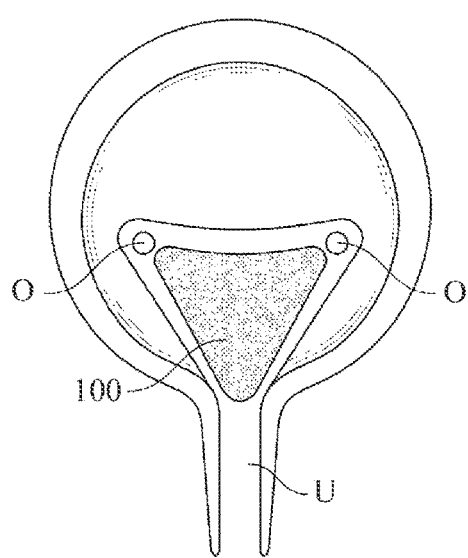

FIG. 17 depicts ablation pattern 100 that encompasses substantially the entire trigone, and advantageously may be generated using devices 40, 60 described above with respect to FIGS. 7 through 12. Such ablation patterns can be used when treating a bladder wall that exhibits larger than typical or more frequent local contractile activity, areas of dense afferent innervation, or areas of target efferent innervation. As will be apparent, combinations of the foregoing described ablation patterns may be beneficially employed. For example, one or more areas of the bladder may be targeted for treatment, including one or more of the following areas, among others: (1) the trigone; (2) the detrusor muscle; (3) the fundus; (4) an apex; (5) the body; (6) the neck; (7) the urethral ostia; (8) the ureteral ostia (one or both); (9) areas of the bladder having unusual morphology or activity, such as areas of denervation or increased local contractile activity or electrical foci; (10) functional areas of the bladder, such as functional muscular units; or (11) areas dense with nervous tissue or where nerves in the bladder wall concentrate to enter/exit the bladder.

In some examples, partial denervation can be beneficial to substantially total ablation. For example, in cases where the patient is observed or measured to have a relatively thin bladder wall, it may be desirable to use a linear crossing pattern for ablation, or to circumscribe the trigone, while retaining areas of intact non-ablated tissue to ensure that an entirely ablate region does not present a risk of rupture immediately post treatment, or that scar tissue does not cause the bladder wall to become unduly rigid after once the ablated region fully heals.

Accordingly, ablation therapy performed in accordance with the present subject matter may be calibrated or controlled to provide partial or specified therapy at a desired position, such as to avoid undesired conditions (e.g., acute urinary retention, post void residual, straining, etc.). For example, in the particular case of nerve ablation proximate the bladder wall, it may be advantageous to achieve only a portion of denervation in a particular region. Partial denervation can include substantially 100% denervation of a particular area or any desired subrange, such as 70-90%, 60-80%, 50-70%, 40-60%, etc. Therapy also may be limited to a particular area, including specific dimensions or surface areas of treatment (e.g., 4-5 square centimeters, extending not more than 1 cm beyond the border of the trigone, etc.). Alternatively or in addition, the extent of treatment may be defined relative to particular patient anatomy (e.g., 80% of the area of the trigone).

As will be readily appreciated by those familiar with ablation technologies, the degree of therapy may be controlled by controlling the density of a pattern of energy delivery. For example, a pattern of lesions that include both ablated zones and non-ablated zones (e.g., 75% ablated and 25% non-ablated, etc.) may be selected or defined to produce a desired degree of therapy. Further, the degree of therapy may be controlled by a limited time and duration of therapy. The amount of damage (e.g., damage to nerves, muscle, etc.) can be correlated to specified therapy parameters, such as time, temperature, frequency, amplitude, etc.

As noted above, the degree of therapy also may be controlled by limiting the layers of tissue affected. For example, the therapy can be limited to not extending beyond certain specific depths or specific anatomic layers of the bladder wall. For example, therapy may be targeted to treat deep layers of the bladder wall, such as the muscle and serosa OR ADVENTITIA, while protecting one or more layers proximate the body of the bladder, such as the glycosaminoglycan layer, mucosa, urothelium, the surface cell layer of the epithelium, intermediate cell layer of the epithelium, etc. Other combinations of layers may be targeted for therapy or protected, for example, by protecting non-targeted tissue using a cooling balloon or other device or method to remove heat.

More specifically, it may be desirable to include a capability to cool the bladder wall tissue directly in contact with the energy delivery element, so as to avoid damaging the mucosa. Devices constructed in accordance with the present subject matter therefore may include features designed to protect selected structures from inadvertent damage, such as the ureteral and urethral ostia. While this may be accomplished by a variety of algorithms and controls (e.g., measuring electrode temperatures, measuring tissue temperatures or impedances, timers, visual feedback, etc), it may in addition be advantageous to use a large thermal mass to moderate temperatures except at the desired location. Examples include the use of a heat sink, such as fluids (e.g., water, saline, etc.), which may be heated or cooled to a temperature distinct from room temperature. Such a heat sink may be either static (e.g., an inflated balloon) or dynamic (e.g., fluid flowing in an open or continuous loop).

For example, a balloon may be filled with a continuously circulating flow of chilled (e.g., using ice-water bath) saline mixed with contrast media and used to cool tissues in direct contact with the balloon, while allowing an internal microwave antenna or other energy delivery element to therapeutically heat underlying tissues. In this manner, at least a portion of the mucosa of the bladder can be protected while treating one or more portions of the underlying or adjacent bladder tissue, such as the basement membrane, suburothelium, submucosa, lamina propria, muscle, adventitia, or serosa.

As a further example, a ureter may be protected, such as by inserting a catheter, a cooling balloon, or other cooling device proximate to or into the ureter prior to or concurrently to treating proximate bladder or nerve tissues. For example, the device may be configured so that its distal tip is positioned within the ureter, and delivers thermal energy to target tissue (e.g., nervous tissue innervating the trigone proximate the ureter, etc.) from the energy delivery element while the distal tip of the device concurrently cools at least a portion of the ureter (e.g., an interior of the ureter) to prevent damage to the ureter from the thermal energy.

It should be understood that in the case of cryotherapy, a heat sink may be used to heat non-target tissues rather than remove heat from the non-target tissue. For example, an ablation device constructed in accordance with the principles of the present subject matter and using a cryogenic probe may include a flow of warmed saline through channels along the shaft of the device to prevent cold damage to the urethra and to localize the cold to the cryogenic probe.

In still other examples, a thermal mass, such as sterile saline, may be introduced into adjacent body spaces, such as the peritoneum, to inhibit or prevent the inadvertent spread of energy delivered during therapy. For example, sterile normal saline may be introduced into the peritoneum to expand the abdomen and create a buffer between the bladder and the intestines. A thermal mass also may be introduced into the rectum, vagina, or uterus either free-flowing or encapsulated in a balloon. Further, a cooling device may be inserted into the bladder if the energy delivery element is in a different location (e.g., in the vagina, etc.). Saline, polymer, gel, or gas also may be added to the pelvis between the anterior wall of the vagina and the posterior bladder wall to increase the distance between these structures prior to the therapy. The uterus also may be used to shield other structures from potential harm, for example, uterine manipulators may be used to interposition the uterus between the bladder and bowel in order to protect the bowel from injury.

In addition to treating bladder dysfunction, pelvic nervous tissue or nerves also may be targeted for therapy or ablation to treat generalized pelvic pain, including nervous tissue on, within, or proximate the bladder wall, including on or within bladder tissue, such as the lamina propria, suburothelium, submucosa, muscle, serosa, adventitia, connective tissue, perivesical fat, and perivesical fascia. In an example, pelvic nerves suitable for treatment may include the pelvic nerve and its branches, as well as other nerves and their branches in or about the pelvic area, including the bladder. For example, such additional treatment areas in a female patient may include bladder tissue, the space between the posterior bladder wall and the anterior wall of the vagina, or the space between the anterior bladder wall and the transversalis fascia. Such additional treatment areas in a male patient may include at least one of bladder tissue, the space between the posterior bladder wall and the anterior wall of the rectum, the space between the base of the bladder wall and the retroprostatic fascia, or the space between the anterior bladder wall and the transversalis fascia.

Other pelvic nerves may be targeted for treatment to relieve pelvic pain, including nerves and nerve plexuses external to the bladder, such as the vesical nerve plexus, rectal plexus, prostate plexus, inferior hypogastric plexis, pelvic splanchnic nerves, pelvic nerves, pelvic nerve branches, general visceral afferent nerves, sacral parasympathetic fibers, lumbar sympathetic fibers, and fibers arising from the hypogastric plexus In general, pelvic nerves include parasympathetic nerves S2-S4 and their branches, which supply the pelvic plexus, bladder, and sphincters, the sympathetic nerves T10-L2 and their branches, which supply the bladder base, internal sphincter, and proximal urethra, and somatic nerves S2-S3 and their branches, which lead to the pudendal nerve supplying the external sphincter.

Further in accordance with the principles of the present subject matter, a variety of access routes may be utilized to perform the therapies described herein. Examples include open surgical access (e.g., laparotomy) or minimally invasive access (e.g., laparoscopic) to the abdominal cavity, the retropubic extraperitoneal space (the "Retzius space"), and different portions of the bladder (e.g., the dome of the bladder covered by the peritoneum, anterior aspects of the bladder, lateral aspects of the bladder, etc.). Transvaginal, transcervical, transuteral, transurethral, or transrectal access is also possible. FIGS. 18-22 illustrate exemplary views of gaining access to the bladder of a female patient.

Figure 18:
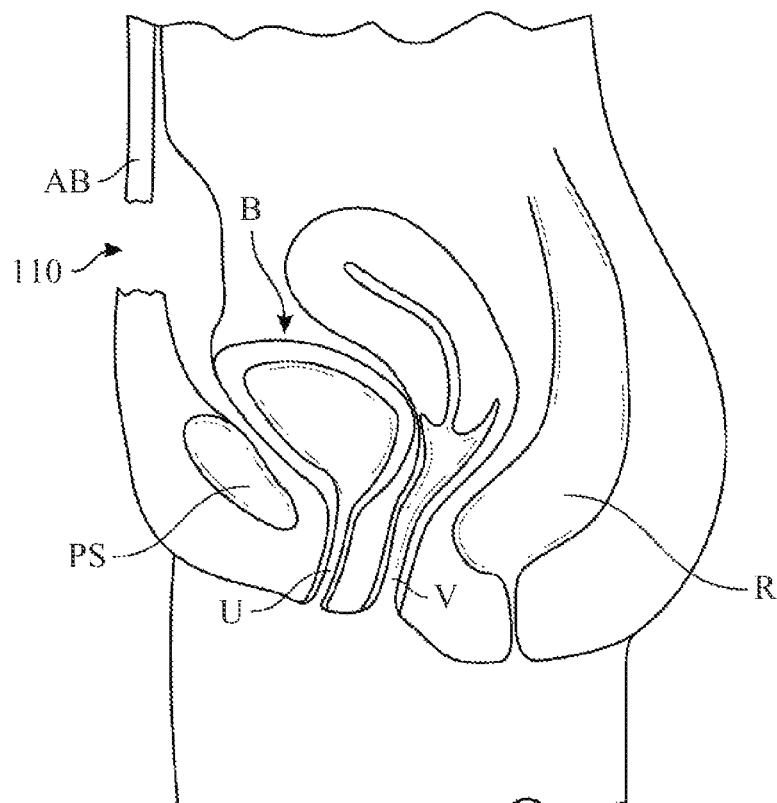
FIG. 18 is a side sectional view of the anatomy of a female abdomen and pelvis depicting abdominal access to the anterior of the bladder.
Figure 19:
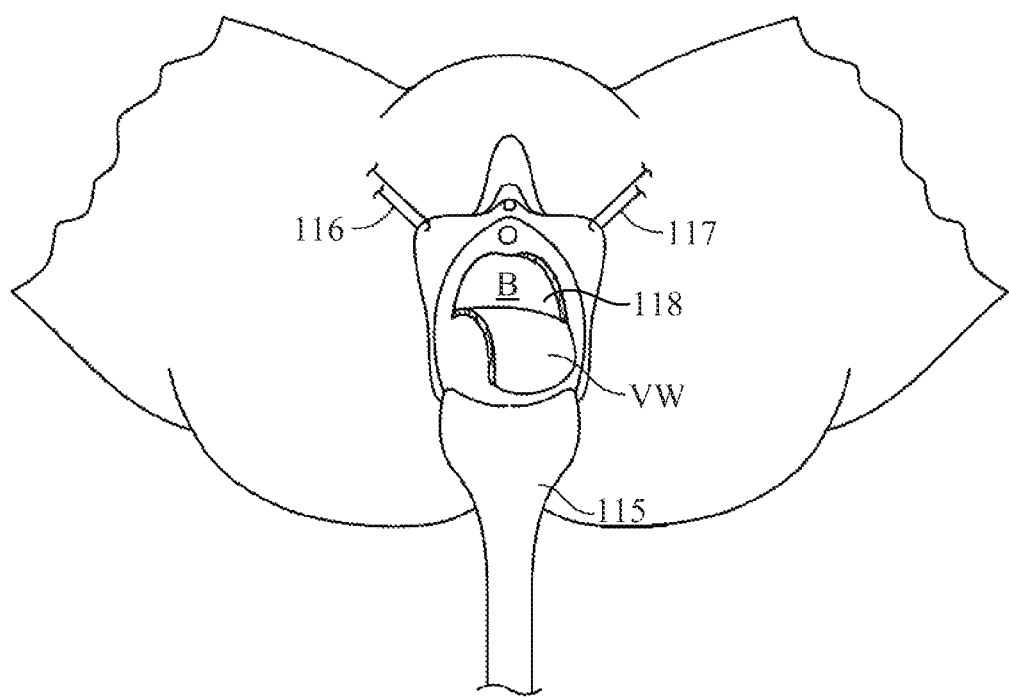
FIG. 19 is a plan view of the anatomy of a female pelvis depicting access to the trigone of the bladder via an opening formed in the anterior vaginal wall.

FIG. 18 is a lateral view of a female pelvis depicting the relative locations of vagina (V), pubic symphysis (PS), rectum (R), bladder (B), and urethra (U), and includes peritoneal or pre-peritoneal dissection through abdominal wall (AB). Incision 110 is be made in abdominal wall, exposing the space of Retzius proximate bladder. The bladder may be directly accessed through incision 110. FIG. 19 depicts a female perineum including vaginal speculum 116 and stay sutures 116, 117 configured to retract and hold open labia minor. The bladder may be accessed through opening 118 formed in anterior vaginal wall (VW).

More specifically, the urinary bladder lies immediately outside of the peritoneum, and is loosely attached to the peritoneum from the apex, across the dome, and down to the vesicouterine pouch. Intraabdominal access allows direct vision of the superior and posterior aspects of the bladder. Dissection of the peritoneum off the abdominal wall develops the Retzius space, which provides direct access to the anterior portion of the bladder lying immediately adjacent to the pubic symphasis. Once the bladder is reached (e.g., from either intraabdominal or extraperitoneal routes), the bladder can be dissected from its lateral and posterior adherents to expose the trigone region or the bladder wall can be incised and later repaired to provide access to the interior of the bladder.

The anterior wall of the vault of the vagina, which lies immediately posterior to the bladder, may be incised to expose the urethra, which is the typical surgical exposure for a transvaginal tape procedure to treat stress incontinence. The transvaginal route is a commonly performed, widely accepted procedure having minimal morbidity. Access to the bladder neck, the trigone of the bladder, or areas off of the midline of the bladder may be provided using a similar, somewhat deeper dissection of the vault of the vagina.

Advantageously, injections into the nerves supplying the trigone may be made both from the interior of the bladder and from the vagina (e.g., lidocaine or other anesthesia injections) to elicit a temporary effect as a screening method prior to denervation.

As will be apparent to a physician of ordinary skill in the art, the female bladder also may be accessed via a conventional laparoscopic procedure or percutaneous suprapubic access via a cannula. Alternatively, percutaneous access to a female pelvis may be established through the perineum, for example, using a cannula to access to the space between the posterior bladder wall and the anterior vaginal wall. Access to the bladder also may be obtained using a conventional cystoscope or other visualization device inserted into the bladder through the urethra, providing viewing access to one or more structures in the bladder, such as the trigone or ureteral ostia. The treatment devices described above may be inserted through a working channel in the cystoscope or alternatively the treatment device may include an imaging system, for example as described as an optional feature of the embodiment of FIG. 7. As described above, the visualization device may be used to position the energy delivery element at a desired position in the bladder and ensure that a safety margin exists between a possible ablation region and one or more features of the bladder, such as the ureteral ostia, ureter, urethra, urethral os, the urethral sphincter, etc. In addition, the visualization device may be configured to provide a cooling function (e.g., chilled saline irrigation, a cooling balloon, etc.).

Use of a combination of access routes may be advantageous. For example, being able to access both sides of a desired tissue target may allow for improved energy density or temperature control at one or more locations. For example, a combination of intravesical and vaginal access may be used to place one or more auxiliary cooling devices (e.g., a balloon inflated with saline) on one or both sides of the desired tissue target to isolate increased temperatures to deeper tissues layers. Further, combining energy delivery from both sides of the desired tissue target may serve to increase temperatures or energy densities in the region of overlap (e.g., deep within the tissue), while minimizing temperatures or densities in the superficial regions (e.g., the bladder glycosaminoglycan layer, urothelium, mucosa, or the vaginal wall). In this manner, therapy advantageously may be directed to desired regions or layers of tissue, while minimizing undesired trauma or injury to other tissue.

Furthermore, where it is intended to use the apparatus and methods of the present subject matter to relieve pelvic pain, pelvic nerves or nervous tissue may be accessed without puncture or incision via navigation through the uterus, laterally through the fallopian tubes, and exiting via the abdominal ostium.

D. Additional Embodiments

In accordance with another aspect of the present subject matter, lesion-creating elements may be combined in structures that aid in creation of desired pattern, such as expanding mesh cages, wire loops, expanding balloons, etc. This portion of the disclosure describes additional examples constructed in accordance with the principles of the present subject matter.

Inflated balloons (e.g., inflated with gas or liquid, such as saline or contrast agent) may be used to provide an integrated heating element (e.g., a microwave antenna, RF electrode, PRF electrode, laser fiber, ultrasound, etc.) at a specific location. In an example, a balloon may be used to centralize an internal microwave antenna (e.g., along an axis of the balloon), or to locate a heating element a specific, known, or desired distance from the desired tissue target (e.g., ranging from zero distance, or contact, to the full diameter of the balloon). One or more balloons may have therapy delivery elements mounted or placed on the exterior of the balloon, such as RF electrodes, RF needles, etc.

For example, an elongated shaft, such as a catheter, configured to be passed through the urethra into the bladder, such as a Foley or one or more other catheters, may include a balloon and an energy delivery device, such as internal microwave antenna, RF electrodes embedded in the wall of the balloon, an inlet/outlet configured to receive or output a heated or cooled gas or fluid, or ultrasound transducer. The energy delivery element may be integrated with the balloon. The balloon may be inflated after urethral insertion and counter-traction applied to bring the balloon into intimate contact with the bladder trigone or bladder neck. In this manner, the energy delivery element will be automatically and reproducibly positioned correctly relative to targeted tissues. In addition, the balloon can be configured to inflate in a desired shape (e.g., cylindrical, ovoid, pancake, arching, triangular, pyramidal, conformable to the surrounding bladder, etc.) so as to facilitate targeting of the desired tissues.

Figure 20:
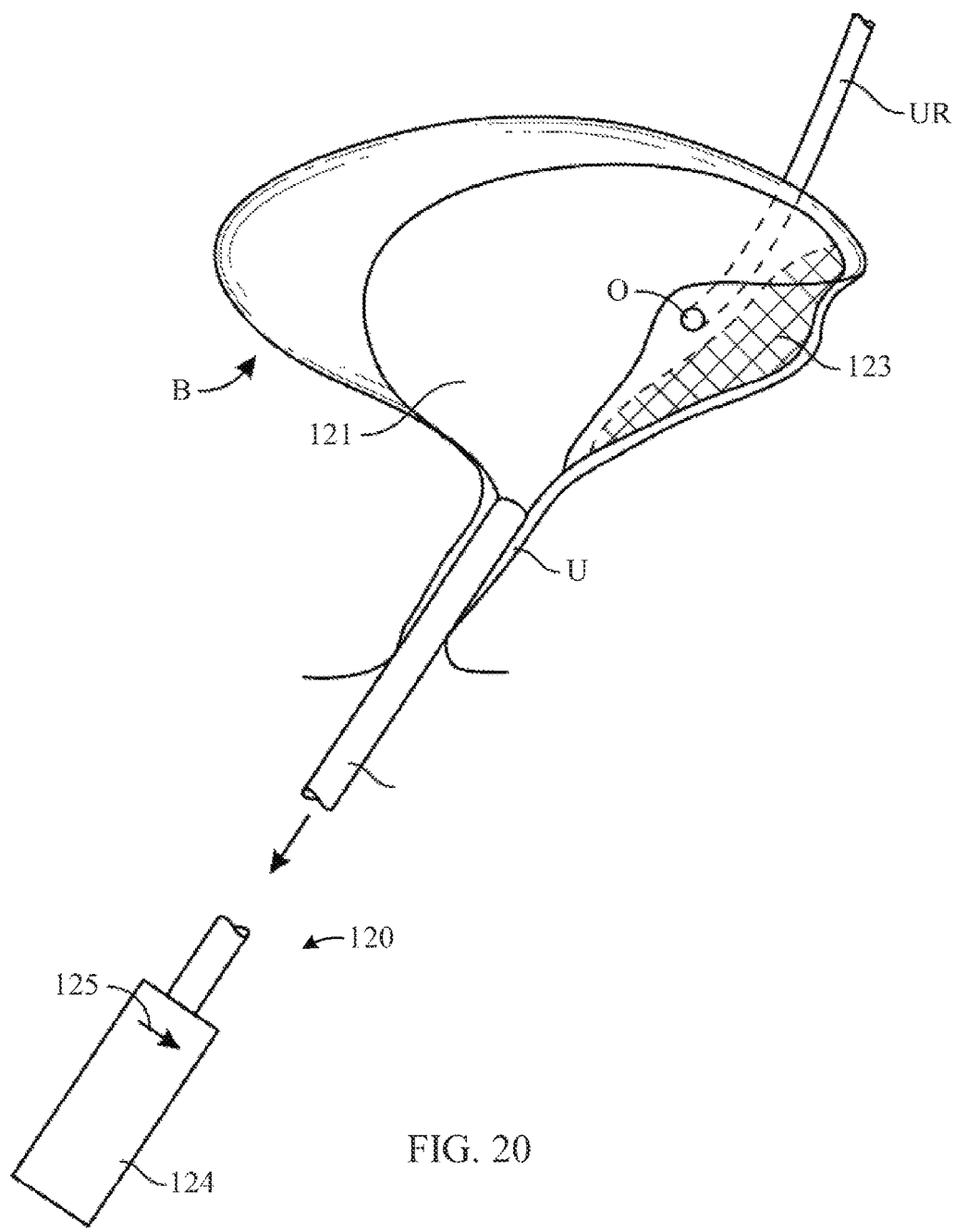
FIG. 20 is a lateral sectional view of a female bladder and urethra depicting an embodiment of apparatus of the present subject matter including an inflatable balloon for positioning an energy delivery element within the bladder.

Referring now to FIG. 20, a lateral view of bladder (B) is shown including device 120 having expandable element 121, such as a balloon, mounted to the distal end of elongated shaft 122. Device 120 illustratively is configured to provide access to bladder through urethra (U). FIG. 20 shows the relative positions of ureteral ostium (O) and ureter (UR).

Expandable element 121 is shown in its expanded deployed state (e.g., for a balloon, an inflated position) and has a reduced diameter state (e.g., for a balloon, a deflated position) that enables it to be advanced through urethra into bladder. Expandable element 121 is coupled to an energy delivery element, as described below. Expandable member 121, in the contracted state may be inserted into bladder through urethra, and then transitioned to the expanded deployed state (as shown in FIG. 20) to position the energy delivery element at a desired position within the bladder, such as between the ureteral ostia. In FIG. 20, the position of the energy delivery element with respect to expandable element 121 is illustrated using by energy delivery zone 123. Expandable element 121 may be configured so that it can be wedged into a specific position in bladder, such as against the trigone, for example, to set the distance between the energy delivery element and the wall of the bladder. Expandable element 121 can include a substantially compliant element configured to conform to the geometry of bladder, a substantially rigid element configured to take a desired shape or to conform at least a portion of the bladder wall to a desired shape, or combinations of both.

If expandable element 121 does not fully fill the bladder, a tension force may be used to seat the expandable element 121 in the neck of the bladder to position expandable element 121 or the energy delivery device at the desired location. The tension force may be applied by a user (e.g., as specified, for example, as directed by the Instructionsfor-Use accompanying device 120), or, in certain examples, by an auxiliary device. For example, device 120 may include a slidable anchor configured to traction expandable device 121 by bearing against the perineum (e.g., where urethra exits the body). The slidable anchor may include a calibration device (e.g., a spring element, etc.) configured to adjust the amount of force applied to the perineum or the bladder.

Illustratively, device 120 includes handle 124 configured to allow a user to position expandable element 121 at the desired position in bladder. The handle may have a fixed position with respect to expandable element 121 or the energy delivery device, and may include indicator 125, such as a marking or a feature (e.g., an arrow), configured to provide information regarding the orientation of expandable element 121 or the energy delivery device to the user. Indicator 125 may include a tactile feature, an accelerometer, audio notification, or one or more other notifications of device orientation.

Figure 21:
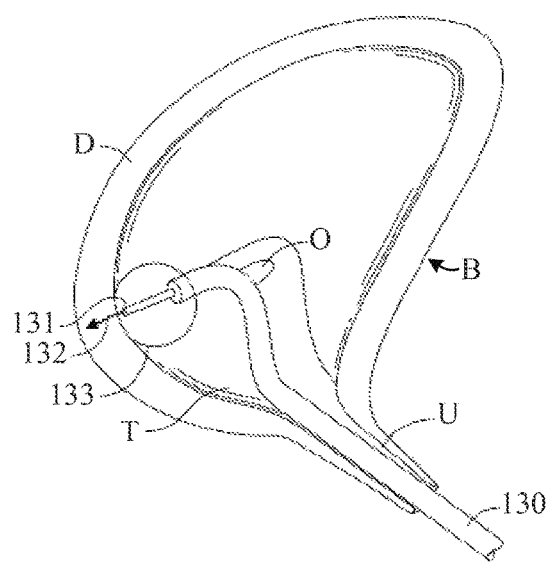
FIG. 21 is a lateral sectional view of a female bladder and urethra depicting a laser embodiment of apparatus of the present subject matter.
Figure 22:
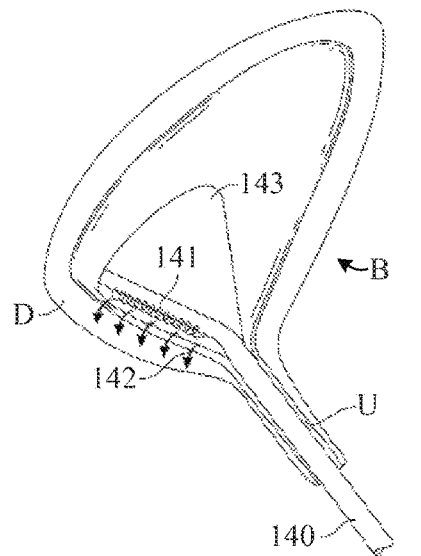
FIG. 22 is a lateral sectional view of a female bladder and urethra depicting a microwave embodiment of apparatus of the present subject matter.

FIGS. 21 and 22 depict lateral sectional views of female bladder (B) including energy delivery devices 130, and 140, respectively, configured to access bladder through urethra (U). FIG. 21 depicts device 130 having a laser energy delivery element including light fiber 131 configured to transmit laser energy 132 to a bladder wall and inflatable balloon 133 proximate to or surrounding light fiber 131. Laser energy 132 may be transmitted to or through at least a portion of the bladder wall or surrounding structure.

In the embodiment of FIG. 21, inflatable balloon 133 is configured to position the energy delivery element a specified distance from the bladder wall, as may be required for proper operation of the energy delivery element or to provide local cooling (e.g., proximate the laser energy 132, such as by removing heat from the target area) to protect tissue proximate inflatable balloon 133. For example, inflatable balloon 133 may be sized to protect specific layers of the bladder wall from damage (e.g., glycosaminoglycan layer, mucosa, urothelium, suburothelium, submucosa, lamina propria, muscularis propria, etc.) or to control tissue damage until a certain depth. One or more characteristics of the laser energy (e.g., frequency, amplitude, etc.) may be modulated to control the maximum depth of tissue damage. Although FIG. 21 depicts device 130 positioned near trigone T proximate the posterior bladder wall, distal region 134 of device 130 may be articulitable so that the energy delivery element may be positioned at other locations within or outside the bladder.

Referring now to FIG. 22, device 140 is depicted that includes a microwave energy delivery element, including microwave antenna 141 configured to deliver microwave energy 142 to the bladder wall. Device 140 further includes inflatable balloon 143 proximate to or surrounding microwave antenna 141. Microwave energy 142 is delivered to or through at least a portion of the bladder wall or surrounding structure. Device 140 may be configured to be disposed in other locations within the bladder, and further, inflatable balloon 143 may be configured to position microwave antenna 141 in any desired position (e.g., at a specified location) or to provide local cooling, thereby protecting tissue proximate balloon 143.

Figure 23:
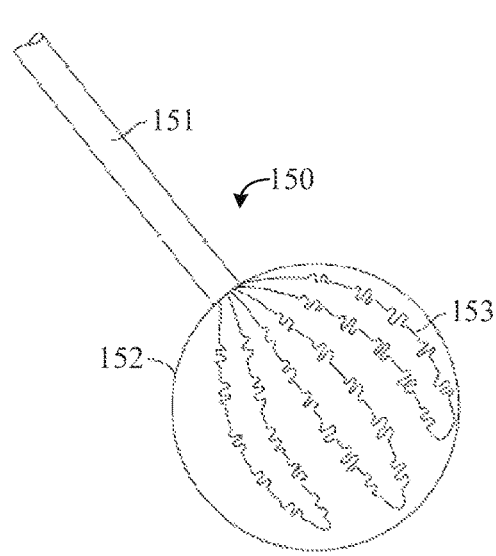
FIG. 23 is a plan view of the distal region of an embodiment of apparatus of the present subject matter wherein the energy delivery element is embedded on an inflatable balloon.
Figure 24:
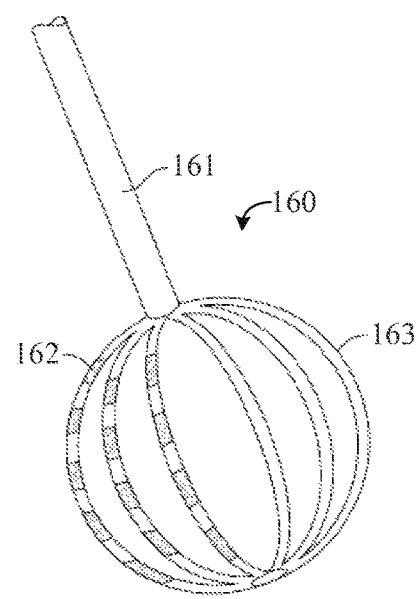
FIG. 24 is a plan view of the distal region of a further alternative embodiment of apparatus of the present subject matter wherein the energy delivery element includes a plurality of electrodes disposed on an expandable wire structure.

Referring now to FIGS. 23 and 24, further alternative examples of apparatus constructed in accordance with the principles of the present subject matter are described. FIG. 23 depicts a distal end of device 150 including elongated shaft 151 having inflatable balloon 152 with energy delivery electrode 153 (e.g., RF electrode, microwave antenna, etc.) embedded in the exterior of balloon 152. FIG. 24 depicts a distal end of device 160 including elongated shaft 161 having plurality of energy delivery elements 162 disposed on expandable wire structure 163. Device 160 is configured so that after expandable wire structure 163 is inserted into the bladder (e.g., such as through the urethra), expandable wire structure 163 may be deployed to urge plurality of energy delivery elements 162 against a desired portion of the interior of the bladder.

Further alternative examples of devices configured to be inserted into the bladder may include other expandable structures, such as linkages, deflectable catheters, mesh cages, shape memory structures, with or without a balloon, that may be inserted into the bladder (e.g., via the urethra or a suprapubic catheter) in a contracted state, and then expanded to form two or three dimensional shapes within the bladder. Such expandable structures may be configured to conform to desired target tissues or areas. Expanding structures also may be positioned proximate an outside bladder wall and used to form two or three dimensional shapes configured to conform to desired target tissues or areas on or proximate to the outside bladder wall. For example, a device penetrated into the perineum or inserted through the vagina, along a course substantially parallel to the posterior bladder wall, may include a variety of deployable needles, for example, to form a desired pattern. In addition to locating the energy delivery element with respect to a target tissue, expandable structures or balloons also may be used to mount multiple energy delivery elements and to control the relative positions of these elements. For example, patterns of therapy delivery may be created either through the simultaneous or sequential activation of the multiple therapy delivery elements.

As discussed above, devices constructed in accordance with the principles of the present subject matter advantageously may incorporate some degree of steerability to position the energy delivery elements relative to desired treatment target locations. Steering may be passive (e.g., a pre-curved device that can be straightened to pass it up the urethra), active (e.g., a catheter that curls, such as based upon tensioning of an integral pull-wire), via a separate auxiliary device (e.g., an external delivery sheath), external magnetic field (Stereotaxis), or employ the shape-memory aspects of certain alloys (e.g., nickel titanium (Nitinol), etc.).

Figure 25:
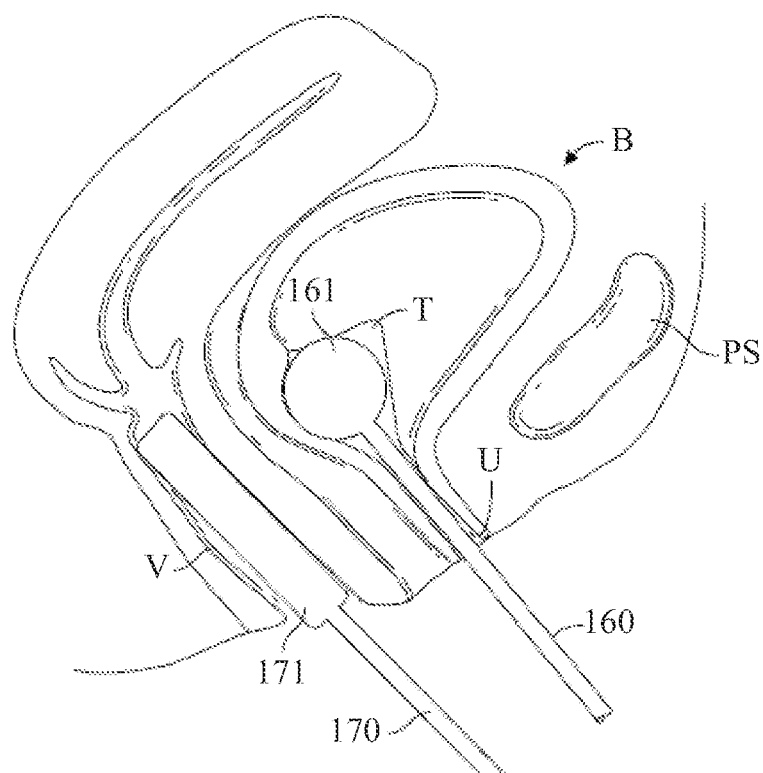
FIGS. 25 and 26 are lateral sectional views of a female pelvis including cooling devices used in conjunction with the energy delivery apparatus of the present subject matter.
Figure 26:
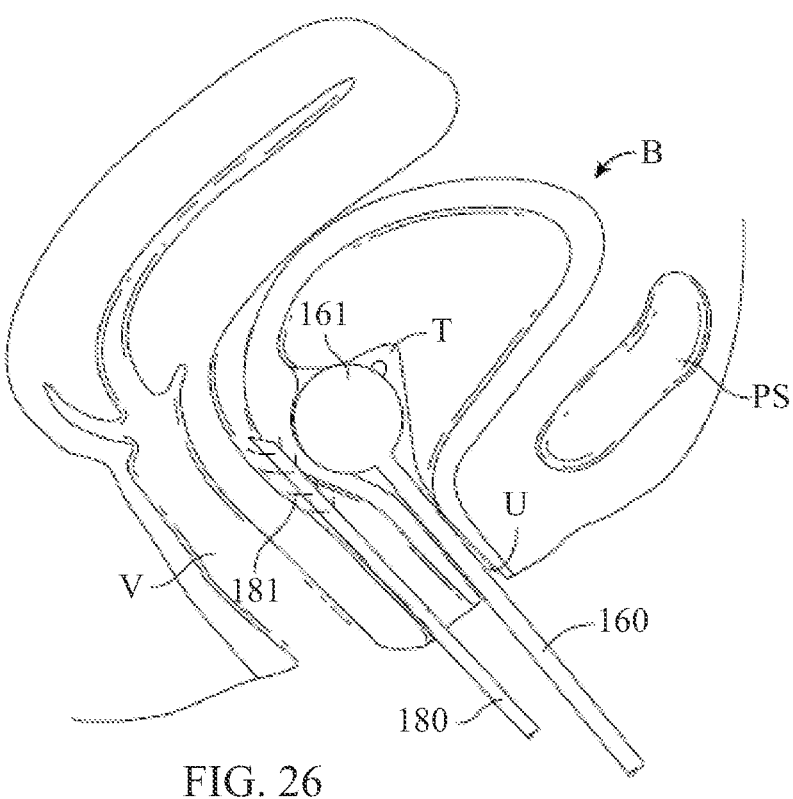

FIGS. 25 and 26 provide lateral section views of a female pelvis including device 160, which illustratively may consist of devices 150 or 160, inserted into bladder (B) through urethra (U). The relative locations of bladder (B), vagina (V), pubic symphysis (PS), and urethra also are shown. In each of FIGS. 25 and 26, device 160 includes inflatable balloon 161 (or an expandable wire structure) configured to be inserted into bladder through urethra in a contracted state and then inflated or otherwise deployed in bladder. For example, device 160 may be configured to provide either heat or cold to tissue of or proximate to bladder, vagina, or other location. Inflatable balloon 161 (e.g., a heat sink) may be configured to remove heat from or to provide heat to at least a portion of the bladder, such as at least a portion of trigone (T) of the bladder. Alternatively, cooling device 161 may include one or more other energy delivery components, such as electrodes, ultrasound transducer, microwave antenna, PRF antenna, or RF antennas, etc., configured to provide thermal energy to tissue within or proximate to a bladder wall.

FIG. 25 depicts auxiliary cooling device 170 including balloon 171 that is configured to remove heat from or to provide heat to at least a portion of vagina. FIG. 26 includes cannula 180 having plurality of needle electrodes 181 that may be selectively deployed within or proximate to the bladder wall (and similar in construction to the needle electrodes described with respect to the embodiment of FIGS. 11 and 12). Needle electrodes 181 may be configured in a bipolar or monopolar arrangement. Needle electrodes 181 also may be configured to be inserted within or through at least a portion of the bladder wall.

The ability for the physician to directly visualize the bladder or other structures during therapy may be beneficial. As discussed for preceding examples, the energy delivery element may be configured to be used within a working channel of a cystoscope or other visualization element, either rigid or flexible. Alternatively, device carrying the energy delivery element may incorporate a visualization element (e.g., lens and fiber optic, CCD chip, light source, etc.). Such a visualization element may either be disposable or a re-usable element that is coupled to a disposable energy delivery device prior to use. Such devices also include fiducial markings or measurements, auxiliary measuring tools, engage anatomic landmarks, or provide tactile feedback to assist the physician during positioning and use of the device.

E. Adjunctive Therapies

Several procedures can serve as useful adjuncts to improve the permanence of the relief sought to be provided by the apparatus and methods of the present subject matter. For example, a prior successful round of botulinum toxin therapy or anesthetic injection (e.g., lidocaine, etc.) may be used to isolate or screen a likely "responder" to the proposed therapy. For example, if a patient's symptoms improve with a transient intervention, then that patient may be a good candidate for an ablation procedure of the tissue using the apparatus and methods described in the present disclosure. If the patient's symptoms do not improve or worsen with the transient intervention, then that patient may not be a good candidate for an ablation procedure that targets the anesthetized tissue.

As a convenient screening tool, lidocaine and other anesthetics have the advantage that their affects wear off after a period of hours instead of a period of 6 to 9 months observed for botulinum toxin injections. Examples of local anesthetics include lidocaine, prilocaine, tetracaine, and benzocaine. The local anesthetic may be applied in the form of a liquid, viscous liquid, spray, or gel.

Alternatively, application of cold (cryoanesthesia) may be used to temporarily numb a desired area, transiently disabling nerve conduction or muscle contractility, and allowing assessment of a patient's symptoms after the intervention until the target tissue rewarms. Examples of cryoanesthesia include liquid nitrogen spray, argon, refrigerant (e.g., Freon), or chilled saline. The cryoanesthesia may be applied either directly to target tissue or contained in a structure, such as a needle, probe, lumen, catheter, balloon, sac, etc.

Dyes or other markers may be used in conjunction with injections to aid in providing permanent or more permanent therapy to the same locations as previous, and successful, injections of a pharmacologic agent. For example, a dye or other marker may include commonly used medical dyes, such as indigo carmine, methylene blue, etc. In addition, more permanent dyes, such as are used in tattoos, may be used when a more durable mark is desired, such as when botulinum toxin is injected into the bladder wall as a screening test.

As a further adjunct to, or in lieu of, the energy delivery modalities disclosed above, it is contemplated that denervation of the bladder may be accomplished or rendered more permanent by mechanically disrupting afferent nervous tissue within the bladder wall. First, nerves of the bladder may be accessed, such as using balloon dissection of the space lateral to the bladder to dissect the peritoneum from the abdominal wall along natural tissue planes in variations of laparoscopic surgery. For example, a dissection balloon may be mounted on an atraumatic probe and tunneled along the lateral border of the bladder. An auxiliary light source within the bladder (e.g., inserted via the urethra) may facilitate this procedure by providing transillumination that aids the tunneling process. The probe also may include technology to visualize and aid in following of the natural tissue planes.

Second, the durability of the denervation may be improved by delaying or preventing nerve regrowth. This may be accomplished by surgically implanting a physical barrier into the space dissected, ablated, destroyed, or otherwise damaged to denervate the bladder (e.g., the lateral aspect of the bladder). Suitable materials for such barriers may include polypropylene mesh, polytetrafluoroethylene (PTFE) or expanded PTFE films, adhesion barriers, hyaluronic acid membranes (e.g., Seprafilm® by Genzyme®, indicated as an adhesion barrier for the pelvis), polyethylene glycol (PEG), injections or deposits of liquid hyaluronic acid, and other polymers or hydrogels. The barrier also may include biologic materials, such as collagen, pericardium, mucosa (intestine), fibrin, etc., such as after suitable processing for sterility and to render these materials non-immunogenic.

Chemical treatments, such as corrosive or cytotoxic chemicals, also may be used to coat or inject the dissected or otherwise damaged areas so as to kill or deactivate exposed nerves. Suitable chemicals may include caustic chemicals (e.g., sodium hydroxide, potassium hydroxide, caustic pencils, etc.), alkalis, strong acids (e.g., sulfuric acid, nitric acid, hydrochloric acid, etc.), concentrated solutions of weaker acids or bases (e.g., formic acid, acetic acid, etc.), Lewis acids (e.g., anhydrous aluminum chloride, boron trifluoride, zinc chloride, etc.), strong oxidizing agents (e.g., hydrogen peroxide), other corrosive chemicals, and neurotoxins.

Additionally, fixative agents, such as glutaraldehyde, formaldehyde/formalin, alcohols, mercuric chloride, potassium dichromate, sodium sulfate, concentrated sugars, etc., may be used to stabilize and strengthen tissues. Capsaicin or other members of the vanilloid family may be used to affect the nerves. Additionally, fixatives (e.g., zinc chloride paste) may be used during or prior to denervation, and applied topically (e.g., to the mucosa from inside the bladder) or injected into the bladder wall.

Chemical agents also may be used such as in conjunction with surgical or energy delivery denervation described above, either to extend the durability of the denervation or to block pain. To prevent the inadvertent dispersion of the chemical agent, it may be delivered as a gel, foam, paste, solid, or other non-liquid form.

As a still further adjunct to the ablation apparatus and methods described above, or as an alternative to such approaches, it is hypothesized that bladder dysfunction may be treated by reducing the elasticity of selected portions of the bladder, such as the trigone, to reduce activation of stretch receptors located in that region. In particular, the bladder trigone is a smooth triangular region of the internal urinary bladder formed by the two ureteral orifices and the internal urethral orifice. The trigone is densely innervated, including terminal branches of the pelvic nerve, and is sensitive to expansion, pressure or change in pressure, signaling the brain that the bladder needs to be emptied. The trigone is of different embryologic origin than the rest of the bladder, as it is derived from the caudal end of mesonephric ducts of mesodermal origin, as the rest of the bladder is of endodermal origin. In females, the mesonephric ducts regress, causing the trigone to be less prominent, but still present.

More specifically, it can be hypothesized that stretch receptors in the trigone are responsible for the sensation of urgency that is the hallmark of overactive bladder. It is further hypothesized that bladder distension during filling is largely confined to the dome of the bladder, which is free of attachments, while the trigone region's local stretch is restricted by the natural attachments of the three lumens and the attachments of the trigone to the underlying vagina (e.g., in the female) or prostate (e.g., in the male). Upon substantial filling, stretch of the dome begins to be transmitted to the relatively stiff trigone, giving the sensation of fullness in a patient, which eventually sharpens to urgency. In the symptomatic overactive bladder patient, uncontrolled detrusor muscle contractions may cause stretch in the trigone region, causing a sensation of urgency even at low bladder volumes.

To address the foregoing phenomenon, it is hypothesized that isolating the trigone region, or other region sensitive to filling, from stretch (e.g., due to non-volitional detrusor muscle contractions) may suppress abnormal sensations of urgency. Similarly, providing additional support to the trigone region may aid its natural contraction during the filling phase and delay funneling of the bladder neck, which can initiate progressive continued micturation. Conceptually, this theory of urge incontinence and overactive bladder may be likened to a circle can be drawn on the side of a partially inflated balloon. Further inflating the balloon results in an increase in the diameter of the drawn circle, which illustrates the additional stretch applied to the balloon. If instead a physical ring of specified diameter were glued to the side of the balloon, further inflation of the balloon would not result in further expansion of the encircled portion of the balloon. Thus, the area of the balloon within and immediately adjacent to the ring effectively is isolated from the increasing volume or stretch of the balloon. Likewise, if a physical bar were attached to the side of a partially inflated balloon, increased inflation of the balloon would result in some increased stretch of the balloon material, especially in a direction orthogonal to the axis of the physical bar. However, the stretch of the balloon would be limited in the region immediately adjacent to the physical bar, especially in a direction parallel to the axis of the physical bar.

Analogously, the inventors hypothesize that implanting a device within the bladder wall will stiffen tissues, either by the implant itself or by the buildup of scar tissue (e.g., a healing response, etc.) that encapsulates the implant. Accordingly, bladder dysfunction may be treatable by modifying the mechanical properties (e.g., stiffness or strengthen) of tissues that reduce stretch in adjacent or circumscribed regions.

In accordance with this aspect of the present subject matter, an implant, such as a suture, may be used to isolate the trigone region from stretch resulting from filling of the bladder. The suture may include a running "purse string" suture that encircles the trigone region to limit the stretch of the trigone by having the suture bear at least a portion or the entire load from bladder expansion. Such a "purse string" suture need not be continuous or even form a complete circle to reduce the stretch of the trigone during bladder filling. For example, several linear suture lines could substantially surround the trigone, while gaps could be left at certain locations (e.g., in areas near delicate structures to be avoided, such as the ureters, the urethra, etc.) to prevent inadvertent damage. In some cases, it may be desirable to leave at least one gap or space to allow for some stretch of the trigone for normal urinary function.

As a further embodiment, reinforcing the trigone itself is possible. For example, one or more lines of suture placed across the trigone, either or both parallel or transverse to the axis of the urethra, may serve to stiffen it. Off axis (e.g., neither parallel nor perpendicular to the urethra) orientations or combinations of orientations (e.g., an 'X' shape) also may offer other advantages. Other patterns, including weaves or combinations of elements, may be useful.

In addition, other support structures may be used to support or isolate the trigone, or to reinforce the trigone from the exterior of the bladder. For example, a polypropylene or other artificial mesh or patch may serve as a mechanical buttress for weakened tissues or as a scaffold that elicits ingrowth of new tissue that locks the mesh in position and adds to the strength of the healed structure. A prosthetic mesh or patch may be implanted at the location of the trigone, either within the detrusor muscle or just external to the bladder in the vesicovaginal potential space. Furthermore, such support structure may be affixed to the interior of the bladder wall where, in addition to preventing stretch, it prevents activation of pressure sensory nerves. Flexible, substantially rigid, or rigid structures (e.g., a rigid bar, etc.), or combinations thereof, may be implanted in intra-detrusor muscle or vesicovaginal locations to reinforce the detrusor muscle. As with the suture lines described above, such bars may either encircle the trigone or cross it in various combinations or permutations. Woven polyester mesh also may be used to stiffen the trigone.

As a further embodiment, an injectable agent may be inserted within a desired plane of tissue. This injectable agent can be configured to "cure" or harden in situ to yield a stable element. Examples of cures include chemical reactions (e.g., RTV silicone, epoxy, etc.), light activations (e.g., commonly blue light or UV, etc.), thermoset, etc. Chemical agents that cause fibrosis or tissue stiffening via other mechanisms, such as via body response to the agent, also may be injected or otherwise applied to the target region of the bladder wall or adjacent tissue. Such agents may include sclerotherapy agents used to scar blood vessels, such as sodium tetradecyl sulfate, polidocanol, etc. The sclerosant may be applied in liquid, foam, gel, or paste form. Other suitable agents include dextrose solution, similar to that used in prolotherapy of ligaments and tendons or platelet rich plasma (PRP) in a gel or graft matrix preparation to stimulate collagen ingrowth.

The support structures described in the preceding paragraphs may be used in combination to provide relief. For example, an injectable agent may be combined with a mesh or other support structure for tissue ingrowth and anchoring. The combined support structure may range from mesh coverings of discrete bars to structures analogous to battens used in sails, where the support structure is mostly a membrane (e.g., mesh, etc.) having relatively small stiffeners (e.g., rigid bars, etc.) interspersed. For example, two or more substantially parallel bars may be arranged across or from borders of a mesh panel.

Support structures described above may be configured as a full or partial ring, including as arcuate segments, semicircles, or rings with a gap, such as like the capital Greek letter omega ($\Omega$). Such full or partial rings may be mated with a mesh panel, such as using the ring to form a border for the mesh that provides stiffness and ease of insertion, while the mesh serves to hold the ring in place, both acutely and after tissue ingrowth.

Surgical access from the vaginal anterior wall provides direct access to the urethra and bladder neck, such as typically done during a transvaginal tape procedure for stress urinary incontinence. In an example, deeper dissection posteriolaterally provides access to both sides of the trigone. Accordingly, using this exposure, a partial ring (e.g., a horseshoe, a capital Greek omega, etc.) may be implanted that substantially encircles the entire trigone. This partial ring may be covered by a polypropylene mesh sleeve that serves to prevent erosion or to provide a matrix for tissue ingrowth.

Suitable support structure also may have an inwardly directed bias (e.g., pinching the trigone inwards to further reduce wall stress, etc.). For example, an undersized ring may be implanted that compresses tissue within its circumference. Such a ring may first be placed and then constricted into a smaller opening. While this constriction could be performed intraoperatively, it can also be done some delay after initial implantation (e.g., after the ring has adhered to the surrounding tissue). In addition, the ring could be held in its expanded state by a resorbable material (e.g., a resorbable suture), such that after some period of implantation (e.g., one to four weeks), the resorbable material can degrade and release the ring to collapse to its smaller shape.

It is advantageous to keep foreign bodies outside of the bladder due to the problems with encrustation and stone formation that have been observed when a foreign body is exposed to the urine environment in the bladder. However, to avoid such problems, the foreign body need only to be covered by intact mucosa, and thus, may reside within or outside of the bladder wall. Furthermore, all of the foregoing therapies, when applied to the bladder, should result in either an intact mucosa or a mucosa that can heal without complication.

While the above discussion has been directed toward the reducing stretch of the trigone, it should be understood that the apparatus and methods described herein are not limited to use in the trigone region, but may be beneficially used in other areas of the bladder, including the fundus, the apex, the body, the neck, the dome, the detrusor muscle, etc.

It is contemplated that in addition to implantation of surgical barriers or restrains within the bladder wall, such as described above, it may be possible to induce thermal denaturation of collagen contained within the bladder wall and thereby modify both the physical and mechanical properties of the bladder. In particular, when heated to a temperature in the range of 65-70 deg C., collagen fibrils within tissue begin to break their chemical bonds and transition from a native highly ordered state to a more random orientation which causes the collagen-containing tissue to shrink by up to 50%. The amount of shrinkage experienced by the tissue depends upon the parameters of the heat applied and to the original orientation of the collagen within the tissue. This effect is used therapeutically in orthopedic applications (e.g., shoulder instability), aesthetics (skin tightening, facelifts, etc.), and urology (e.g., stress incontinence). While in the short term, thermal denaturation has been observed to degrade the mechanical properties (e.g., strength) of the tissue, the body's healing response over several weeks results in an ultimately stronger and stiffer structure, replacing elastic tissue with shorter, stiffer, and thicker inelastic fibrotic tissue.

Accordingly, as an adjunct to the energy delivery apparatus and methods described elsewhere in this disclosure, or in lieu thereof, in accordance with yet another aspect of the present subject matter thermal denaturation may be used to locally shrink selected tissues in order to isolate the trigone region from stretch. For example, a circular zone around the trigone may be denatured, thereby providing a constricting ring that reduces or limits stretch within the circumscribed region.

In certain applications of thermal denaturation, especially those where the affected tissue experiences large physiologic loads, initial degradation of tissue mechanical properties in the interval before the body's healing response strengthens the tissue may be of concern, requiring external support (e.g., a splint, etc.) prior to healing. Although physiologic loading of the bladder is relatively small and may not exceed the limits of the tissue even in the immediate post-therapy period, the stretch of a fully inflated bladder may be significant. Accordingly, following thermal denaturation of the bladder, a simple timed voiding (e.g., every hour, etc.) in the immediate post-therapy period may be sufficient to avoid significant stretch. In addition, use of a temporary catheter (e.g., Foley, suprapubic, etc.) may be used for a short time so as to allow for healing in a fully deflated and unstretched bladder.

While collagen denaturation may be used to shrink tissues (e.g., due to the natural tendency of the collagen fibers to shorted when not constrained), collagen also can be molded by heating the tissue to a denaturation point while also holding the tissue in a desired shape or by applying a load. Thus, in an alternative embodiment, the bladder volume may be increased by applying heat to the bladder wall and inflating the bladder to a desired volume or pressure. In this case, the bladder may be expanded with a heated liquid, gel, or pressurized gas, or by using an inflated balloon with heating device. In some cases, a combination of heat and distention may be employed to ablate afferent nervous tissue within the bladder wall, so as to reduce pain or urge sensation.

Expanding the cystometric volume of the bladder may serve several functions. First, some conditions, especially interstitial cystitis (IC) are primarily associated with a constricted bladder volume. Further, increased bladder volume may decrease frequency, one of the hallmark symptoms of overactive bladder. Finally, increasing the bladder volume should serve to decrease wall stress at a given volume, reducing afferent nerve traffic and potentially decreasing overactive bladder. Expanding the volume of the bladder using the collagen remodeling technique described above may be advantageous when compared to previously-known surgical techniques that are used to increase bladder capacity (e.g., detrusor myomectomy, enterocystoplasty, etc.), which are highly invasive procedures involving significant complications and morbidity.

F. Treatment of Chronic Genitourinary Pelvic Pain Syndromes

Pelvic pain disorders involve functional abnormalities of muscle tensioning and relaxation having inflammatory and immunologic components. Pelvic pain disorders are difficult to treat because the pathophysiology is poorly understood. There is no single universally effective therapy available for treatment of this malady. Bidirectional neural cross talk and cross sensitization between the colon, pelvis, and lower urinary tract due to convergence of pelvic pain afferents result in overlap of clinical pain syndromes. These cross organ reflexes help integrate sexual, bowel, and bladder function. However, sensitization of afferent pathways of one viscera by irritation in another viscera may play a role in pelvic pain syndromes.

Chronic female pelvic pain syndromes include pain related to conditions that affect the reproductive tract (e.g., endometriosis, pelvic inflammatory disease, vulvodynia, vaginismus, dyspareunia, etc.), levator ani pain, or irritable bowel syndrome. Previously known treatments typically include antidepressants, anxiolytics, gabapentin, local anesthetic injections, steroids, pelvic floor exercises, dietary changes, or soft tissue mobilization.

Chronic male pelvic pain syndromes include perineal, lower abdominal, testicular, penile, scrotal, or testicular pain, and is the most common form of prostatitis. In addition to pain, urinary symptoms and pain with ejaculation may accompany prostatitis. Previously known therapies typically include symptomatic treatment with a variety of anti-inflammatory medications, anesthetics, analgesics, or muscle relaxants, as well as therapies aimed at treating presumed etiologies, such as infection (e.g., antibiotics) or obstruction (e.g., alpha adrenergic blockade). Also, botolinum toxin may improve voiding dysfunction and pain in some of these patients.

Painful bladder syndrome, or interstitial cystitis, involves chronic lower urinary tract irritative symptoms (e.g., urinary urgency or frequency) and pelvic pain in the absence of other pathology. Painful bladder syndrome affects both men and women and is often associated with increased pain with bladder filling, which is often extreme in severity during flare-ups. Neuroplasty due to enhanced activation of nociceptive afferent pathways can result in prolonged pain responses and spread of the pain to previously uninvolved neurons.

Previously-known drug therapy for painful bladder syndrome generally aims at a variety of potential etiologies, including bladder irrigation with hyaluronic acid, heparin, or vallinoids (e.g., resiniferatoxin), suppressing mast cell histamine release using antihistamines, or modulation of neurosensory activity with oral drugs, such as amitryptiline, duloxetine, gabapentin, or topiramate. Although botulinum toxin delivered by injection into the bladder wall or instillation into the bladder has been observed to transiently improve symptoms, there typically is a 7 to 30 day delay prior to maximal effect, with waning efficacy. In spite of these therapies targeting a variety of mechanisms, a large number of patients with painful bladder syndrome still require narcotic use to help them tolerate the pain.

In spite of the long list of therapies used to treat patients suffering from chronic genitourinary pelvic pain syndromes, these therapies are often not optimally effective, have side effects or risks, or lack good prospective data to support their use. The present inventors believe that the apparatus and methods described in this disclosure advantageously may be used to reduce discomfort and improve function in certain patients with a chronic genitourinary pelvic pain, without requiring drugs, which can have systemic side effects, and without the need to perform an invasive injection or surgical procedure. More specifically, the present inventors hypothesize that certain of the examples described above for treating bladder dysfunction beneficially may be used in the treatment of three general categories of chronic genitourinary pelvic pain syndromes: (1) chronic female pelvic pain syndromes; (2) chronic male pelvic pain syndromes; (3) and painful bladder syndrome. It is believed that the energy delivery apparatus and methods described above may be used to ablate nervous tissue, reduce muscle mass, muscle contractility, paralyze muscle, or stun muscle, thereby affording relief from the above pelvic pain and painful bladder syndromes.

In accordance with this aspect of the subject matter, the energy delivery apparatus and methods described elsewhere in this disclosure may be used to disrupt, reduce, interfere, or modulate conduction of afferent receptors (e.g., tension receptors, nociceptors, etc.), axons, neurons, nervous tissue, nerve fibers (e.g., unmyelinated C fibers or myelinated A-delta fibers), nerves, nerve branches, nerve signals, ganglia, ganglion cells, myofibroblast cells, or pathways of the lower urinary tract, suburothelium, submucosa, lamina propria, adventitia, perivesical fat, vulva, vagina, cervix, uterus, fallopian tubes, genitourinary system, pelvic floor, rectum, colon, or pelvis. The energy delivery apparatus and methods of the present subject matter also may be used to disrupt, reduce, interfere, or modulate conduction of efferent receptors, axons, neurons, nerve fibers, nerves, nerve branches, nerve signals, ganglia, ganglion cells, myofibroblast cells, or pathways of the lower urinary tract, suburothelium, submucosa, lamina propria, vulva, vagina, cervix, uterus, fallopian tubes, genitourinary system, pelvic floor, rectum, colon, or pelvis.

Afferent or efferent peripheral nerves that can be targeted for therapy may include sacral parasympathetic (e.g., pelvic nerves), thoracolumbar sympathetic (e.g., hypogastric nerves and sympathetic chain), and sacral somatic nerves (e.g., pundendal nerves). Target nerves also may include the vesical plexus, prostatic plexus (in men), inferior hypogastric plexus, the uterovaginal plexus (in women), and the pelvic splanchnic nerves. The apparatus and methods of the present subject matter may be used to reduce neural cross talk between organs or to treat pain from multiple sources with one intervention, for example, with a therapeutic energy delivery element inserted through a natural orifice, such as the bladder, urethra, vagina, cervix, uterus, fallopian tube, rectum, colon, or any of the other access routes described elsewhere in this disclosure.

Additional Notes and Examples

Example 1 can include or use subject matter (such as an apparatus, a method, a means for performing acts, or a device readable medium including instructions that, when performed by the device, can cause the device to perform acts), such as an apparatus, such as can include or use an elongated shaft having a distal region; and an energy delivery element sized and shaped to be positioned at a desired position within a bladder and configured to deliver energy to non-superficial target tissue within or proximate to a bladder wall to modulate bladder function while retaining a mucosal surface of the bladder wall superficial to the non-superficial target tissue substantially intact, wherein the distal region of the elongated shaft is configured to position the energy delivery element at the desired position within the bladder.

Example 2 can include or use, or can optionally be combined with the subject matter of claim 1 to optionally include or use the bladder function including at least one of a sense of urge, sense of pressure, incontinence, frequency, nocturia, bladder capacity, or pain.

Example 3 can include or use, or can optionally be combined with the subject matter of one or any combination of Examples 1 or 2 to optionally include or use the desired position within the bladder including a trigone region of the bladder.

Example 4 can include or use, or can optionally be combined with the subject matter of one or any combination of Examples 1 through 3 to optionally include or use the desired position within the bladder including between or below the ureteral orifices.

Example 5 can include or use, or can optionally be combined with the subject matter of one or any combination of Examples 1 through 4 to optionally include or use the energy delivery element being configured to deliver energy to non-superficial target tissue at a substantially uniform distance from the mucosal surface of the bladder to modulate bladder function.

Example 6 can include or use, or can optionally be combined with the subject matter of one or any combination of Examples 1 through 5 to optionally include or use the elongated shaft being configured to remove heat from non-target tissue including the mucosal surface of the bladder wall superficial to the non-superficial target tissue.

Example 7 can include or use, or can optionally be combined with the subject matter of one or any combination of Examples 1 through 6 to optionally include or use the elongated shaft being configured to receive a liquid and to remove heat from non-target tissue using the liquid.

Example 8 can include or use, or can optionally be combined with the subject matter of one or any combination of Examples 1 through 7 to optionally include or use the energy delivery element being configured to modulate nerve traffic to or from at least a portion of the bladder.

Example 9 can include or use, or can optionally be combined with the subject matter of one or any combination of Examples 1 through 8 to optionally include or use the non-superficial target tissue including a pelvic nerve within or proximate to the bladder wall.

Example 10 can include or use, or can optionally be combined with the subject matter of one or any combination of Examples 1 through 9 to optionally include or use the proximate to the bladder wall in a female patient including at least one of the space between a posterior bladder wall and an anterior wall of the vagina, or the space between the anterior bladder wall and a transversalis fascia.

Example 11 can include or use, or can optionally be combined with the subject matter of one or any combination of Examples 1 through 10 to optionally include or use the proximate to the bladder wall in a male patient including at least one of the space between the posterior bladder wall and the anterior wall of the rectum, the space between the base of the bladder wall and the retroprostatic fascia, or the space between the anterior bladder wall and the transversalis fascia.

Example 12 can include or use, or can optionally be combined with the subject matter of one or any combination of Examples 1 through 11 to optionally include or use the energy delivery element including a thermal energy delivery element configured to deliver thermal energy to the non-superficial target tissue within or proximate to the bladder wall to modulate bladder function.

Example 13 can include or use, or can optionally be combined with the subject matter of one or any combination of Examples 1 through 12 to optionally include or use the thermal energy delivery element being configured to deliver thermal energy to ablate the non-superficial target tissue within or proximate to the bladder wall to modulate nerve traffic to or from at least a portion of a bladder.

Example 14 can include or use, or can optionally be combined with the subject matter of one or any combination of Examples 1 through 13 to optionally include or use the energy delivery element including a radio frequency (RF) energy source.

Example 15 can include or use, or can optionally be combined with the subject matter of one or any combination of Examples 1 through 14 to optionally include or use the energy delivery element including at least one of a microwave energy source, a laser energy source, a cryo energy source, an ultrasound energy source, or a mono or bipolar electrocautery energy source.

Example 16 can include or use, or can optionally be combined with the subject matter of one or any combination of Examples 1 through 15 to optionally include or use a heat sink coupled to the distal region of the elongated shaft, the heat sink configured to protect non-target tissue.

Example 17 can include or use, or can optionally be combined with the subject matter of one or any combination of Examples 1 through 16 to optionally include or use the distal region of the elongated shaft including an expandable member configured to position the energy delivery element at the desired position within the bladder.

Example 18 can include or use, or can optionally be combined with the subject matter of one or any combination of Examples 1 through 17 to optionally include or use an indicator configured to provide information indicative of the orientation of the energy delivery device in the bladder.

Example 19 can include or use, or can optionally be combined with the subject matter of one or any combination of Examples 1 through 18 to optionally include or use the expandable member including a balloon configured to remove heat from non-target tissue.

Example 20 can include or use, or can optionally be combined with the subject matter of one or any combination of Examples 1 through 19 to optionally include or use a first surface in the distal region of the elongated shaft, the first surface configured to receive the mucosal surface, wherein the energy delivery element includes a longitudinal portion configured to be disposed in the non-superficial target tissue at a substantially uniform distance from the first surface of the apparatus to provide therapy to the non-superficial target tissue.

Example 21 can include or use, or can optionally be combined with the subject matter of one or any combination of Examples 1 through 20 to optionally include or use the energy delivery element is configured to provide therapy to the non-superficial target tissue at a substantially uniform distance from and along the first surface of the apparatus.

Example 22 can include or use, or can optionally be combined with the subject matter of one or any combination of Examples 1 through 21 to optionally include or use the first surface of the apparatus being configured to grasp and conform the mucosal surface to at least a portion of the first surface of the apparatus.

Example 23 can include or use, or can optionally be combined with the subject matter of one or any combination of Examples 1 through 22 to optionally include or use the first surface of the apparatus including a suction port configured to apply suction to and grasp and conform the mucosal surface to at least a portion of the first surface of the apparatus.

Example 24 can include or use, or can optionally be combined with the subject matter of one or any combination of Examples 1 through 13 to optionally include or use the energy delivery element including a first needle electrode configured to be disposed in the non-superficial target tissue at a substantially uniform distance from the first surface of the apparatus and to deliver energy to the non-superficial target tissue.

Example 25 can include or use subject matter (such as an apparatus, a method, a means for performing acts, or a device readable medium including instructions that, when performed by the device, can cause the device to perform acts), such as a method, such as can include or use delivering energy to non-superficial target tissue within or proximate to a bladder wall to modulate bladder function while retaining a mucosal surface of the bladder wall superficial to the non-superficial target tissue substantially intact.

Example 26 can include or use, or can optionally be combined with the subject matter of one or any combination of Examples 1 through 25 to optionally include or use the delivering energy to modulate bladder function including delivering energy to modulate at least one of a sense of urge, sense of pressure, incontinence, frequency, nocturia, bladder capacity, or pain.

Example 27 can include or use, or can optionally be combined with the subject matter of one or any combination of Examples 1 through 26 to optionally include or use the delivering energy to non-superficial target tissue within or proximate to the bladder wall including delivering energy to non-superficial target tissue within a trigone region of a bladder.

Example 28 can include or use, or can optionally be combined with the subject matter of one or any combination of Examples 1 through 27 to optionally include or use the delivering energy to non-superficial target tissue within or proximate to the bladder wall including delivering energy to non-superficial target tissue within the bladder wall between or below the ureteral orifices.

Example 29 can include or use, or can optionally be combined with the subject matter of one or any combination of Examples 1 through 28 to optionally include or use the delivering energy to non-superficial target tissue to modulate bladder function including delivering energy to non-superficial target tissue at a substantially uniform distance from the mucosal surface of a bladder to modulate bladder function.

Example 30 can include or use, or can optionally be combined with the subject matter of one or any combination of Examples 1 through 29 to optionally include or use removing heat from non-target tissue including the mucosal surface of the bladder wall superficial to the non-superficial target tissue.

Example 31 can include or use, or can optionally be combined with the subject matter of one or any combination of Examples 1 through 30 to optionally include or use the removing heat including receiving a liquid at an elongated shaft to remove heat from non-target tissue.

Example 32 can include or use, or can optionally be combined with the subject matter of one or any combination of Examples 1 through 20 to optionally include or use the delivering energy to modulate bladder function including delivering energy to modulate nerve traffic to or from at least a portion of a bladder.

Example 33 can include or use, or can optionally be combined with the subject matter of one or any combination of Examples 1 through 32 to optionally include or use the delivering energy to non-superficial target tissue including delivering energy to a pelvic nerve within or proximate to the bladder wall.

Example 34 can include or use, or can optionally be combined with the subject matter of one or any combination of Examples 1 through 33 to optionally include or use the delivering energy to non-superficial target tissue within or proximate to the bladder wall in a female patient including at least one of bladder tissue, the space between a posterior bladder wall and an anterior wall of the vagina, or the space between the anterior bladder wall and a transversalis fascia.

Example 35 can include or use, or can optionally be combined with the subject matter of one or any combination of Examples 1 through 34 to optionally include or use the delivering energy to non-superficial target tissue within or proximate to the bladder wall in a male patient including at least one of bladder tissue, the space between a posterior bladder wall and an anterior wall of the rectum, the space between a base of the bladder wall and a retroprostatic fascia, or the space between an anterior bladder wall and a transversalis fascia.

Example 36 can include or use, or can optionally be combined with the subject matter of one or any combination of Examples 1 through 35 to optionally include or use the delivering energy including delivering thermal energy to the non-superficial target tissue within or proximate to the bladder wall to modulate bladder function.

Example 37 can include or use, or can optionally be combined with the subject matter of one or any combination of Examples 1 through 36 to optionally include or use the delivering energy including delivering thermal energy to ablate the non-superficial target tissue within or proximate to the bladder wall to modulate nerve traffic to or from at least a portion of a bladder.

Example 38 can include or use, or can optionally be combined with the subject matter of one or any combination of Examples 1 through 37 to optionally include or use the delivering energy including using a radio frequency (RF) energy source.

Example 39 can include or use, or can optionally be combined with the subject matter of one or any combination of Examples 1 through 38 to optionally include or use the delivering energy including using at least one of a microwave energy source, a laser energy source, a cryo energy source, an ultrasound energy source, or a mono or bipolar electrocautery energy source.

Example 40 can include or use, or can optionally be combined with the subject matter of one or any combination of Examples 1 through 20 to optionally include or use protecting non-target tissue using a heat sink, wherein the protecting includes retaining a mucosal surface of the bladder wall superficial to the non-superficial target tissue substantially intact.

Example 41 can include or use, or can optionally be combined with the subject matter of one or any combination of Examples 1 through 40 to optionally include or use positioning an energy delivery element at a desired position within the bladder using an expandable member.

Example 42 can include or use, or can optionally be combined with the subject matter of one or any combination of Examples 1 through 41 to optionally include or use the expandable member including a balloon configured to remove heat from non-target tissue.

Example 43 can include or use, or can optionally be combined with the subject matter of one or any combination of Examples 1 through 42 to optionally include or usereceiving the mucosal surface at a first surface of an apparatus, and positioning a longitudinal portion of an energy delivery element in the non-superficial target tissue at a substantially uniform distance from the first surface of the apparatus to provide therapy to the non-superficial target tissue.

Example 44 can include or use, or can optionally be combined with the subject matter of one or any combination of Examples 1 through 43 to optionally include or use the delivering energy including delivering energy to provide therapy to the non-superficial target tissue at a substantially uniform distance from and along the first surface of the apparatus.

Example 45 can include or use, or can optionally be combined with the subject matter of one or any combination of Examples 1 through 44 to optionally include or use grasping a portion of the mucosal surface, and conforming the mucosal surface to at least a portion of the first surface of the apparatus.

Example 46 can include or use, or can optionally be combined with the subject matter of one or any combination of Examples 1 through 45 to optionally include or use the grasping and conforming includes using a suction port configured to apply suction to and grasp and conform the mucosal surface to at least a portion of the first surface of the apparatus.

Example 47 can include or use, or can optionally be combined with the subject matter of one or any combination of Examples 1 through 46 to optionally include or use the delivering energy to non-superficial target tissue including: positioning a first needle electrode in the non-superficial target tissue at a substantially uniform distance from the first surface of the apparatus; and delivering energy to the non-superficial target tissue using the first needle electrode.

Example 1A can include or use subject matter (such as an apparatus, a method, a means for performing acts, or a device readable medium including instructions that, when performed by the device, can cause the device to perform acts), such as an apparatus, such as can include or use a device sized and shaped to be inserted into a bladder through a urethra, the device including: an elongated shaft having a distal region; a first surface in the distal region of the elongated shaft, the first surface configured to receive a mucosal surface of a bladder wall superficial to a target volume; and a therapy delivery element having a longitudinal portion configured to be disposed in the target volume at a substantially uniform distance from the first surface of the device to provide therapy to the target volume.

Example 2A can include or use, or can optionally be combined with the subject matter Examples 1A to optionally include or use the therapy delivery element being configured to provide therapy to the target volume at a substantial uniform distance from and along the first surface of the device.

Example 3A can include or use, or can optionally be combined with the subject matter of one or any combination of Examples 1A through 2A to optionally include or use the therapy delivery element being configured to provide therapy to the target volume while retaining the mucosal surface of the bladder wall superficial to the target volume substantially intact.

Example 4A can include or use, or can optionally be combined with the subject matter of one or any combination of Examples 1A through 3A to optionally include or use the therapy delivery element being configured to provide therapy to the target volume at least 2 mm from the first surface of the device.

Example 5A can include or use, or can optionally be combined with the subject matter of one or any combination of Examples 1A through 4A to optionally include or use the first surface of the device being configured to grasp and conform the mucosal surface to at least a portion of the first surface.

Example 6A can include or use, or can optionally be combined with the subject matter of one or any combination of Examples 1A through 5A to optionally include or use the first surface of the device includes a suction port configured to apply suction to and grasp and conform the mucosal surface to at least a portion of the first surface of the device.

Example 7A can include or use, or can optionally be combined with the subject matter of one or any combination of Examples 1A through 6A to optionally include or use a suction source configured to provide suction to the suction port.

Example 8A can include or use, or can optionally be combined with the subject matter of one or any combination of Examples 1A through 7A to optionally include or use the first surface of the device including a plurality of suction ports configured to apply suction to and grasp and conform the mucosal surface to at least a portion of the first surface of the device.

Example 9A can include or use, or can optionally be combined with the subject matter of one or any combination of Examples 1A through 8A to optionally include or use the first surface of the device being configured to receive an external force, the external force configured to conform the mucosal surface to at least a portion of the first surface of the device.

Example 10A can include or use, or can optionally be combined with the subject matter of one or any combination of Examples 1A through 9A to optionally include or use the first surface of the device defining a first plane.

Example 11A can include or use, or can optionally be combined with the subject matter of one or any combination of Examples 1A through 10A to optionally include or use the distal region of the elongated shaft including a first lumen and a first opening at a distal end of the first elongated shaft, at least a portion of the first lumen and the first opening defining a second surface, wherein the device includes a second portion distal to the first longitudinal portion, the second portion including the first surface of the device, the first surface of the device being a substantially uniform distance from the second surface.

Example 12A can include or use, or can optionally be combined with the subject matter of one or any combination of Examples 1A through 11A to optionally include or use the therapy delivery element including a first needle electrode moveable in the first lumen and extendable out of the first opening, the first needle electrode configured to be disposed in the target volume at the substantially uniform distance from the first surface of the device and to deliver energy to the target volume.

Example 13A can include or use, or can optionally be combined with the subject matter of one or any combination of Examples 1A through 12A to optionally include or use the first opening being at the distal end of the first lumen.

Example 14A can include or use, or can optionally be combined with the subject matter of one or any combination of Examples 1A through 13A to optionally include or use the first needle electrode being extendable out of the first opening and into the target volume.

Example 15A can include or use, or can optionally be combined with the subject matter of one or any combination of Examples 1A through 14A to optionally include or use the distal region of the elongated shaft including first and second lumens and first and second openings at a distal end of the first longitudinal portion, at least a portion of the first and second lumens and the first and second openings defining a second surface, wherein the device includes a second portion distal to the first longitudinal portion, the second portion including the first surface of the device, the first surface of the device being substantially parallel to the second surface.

Example 16A can include or use, or can optionally be combined with the subject matter of one or any combination of Examples 1A through 15A to optionally include or use: a first needle electrode moveable in the first lumen and extendable out of the first opening; and a second needle electrode moveable in the second lumen and extendable out of the second opening, wherein the first and second needle electrodes are configured to be disposed in the target volume at the substantially uniform distance from the first surface of the device and to deliver bipolar radio frequency (RF) energy to the target volume.

Example 17A can include or use, or can optionally be combined with the subject matter of one or any combination of Examples 1A through 16A to optionally include or use the therapy delivery element being configured to provide thermal energy to the target volume at the substantially uniform distance from and along the first surface of the device.

Example 18A can include or use, or can optionally be combined with the subject matter of one or any combination of Examples 1A through 17A to optionally include or use the therapy delivery element is configured to modulate at least one of a sense of urge, a sense of pressure, incontinence, frequency, nocturia, bladder capacity, or pain.

Example 19A can include or use, or can optionally be combined with the subject matter of one or any combination of Examples 1A through 18A to optionally include or use the therapy delivery element being configured to modulate nerve traffic to or from at least a portion of the bladder.

Example 20A can include or use, or can optionally be combined with the subject matter of one or any combination of Examples 1A through 19A to optionally include or use the therapy delivery element being configured to provide energy to ablate at least a portion of the target volume.

Example 21A can include or use, or can optionally be combined with the subject matter of one or any combination of Examples 1A through 20A to optionally include or use the device being sized and shaped to be positioned at a desired position within the bladder.

Example 22A can include or use, or can optionally be combined with the subject matter of one or any combination of Examples 1A through 21A to optionally include or use the desired position within the bladder includes at least a portion of a trigone region of the bladder.

Example 23A can include or use, or can optionally be combined with the subject matter of one or any combination of Examples 1A through 22A to optionally include or use the desired position within the bladder including between or below the ureteral orifices.

Example 24A can include or use, or can optionally be combined with the subject matter of one or any combination of Examples 1A through 23A to optionally include or use the first surface including a suction lumen configured to provide suction to the suction port.

Example 25A can include or use subject matter (such as an apparatus, a method, a means for performing acts, or a device readable medium including instructions that, when performed by the device, can cause the device to perform acts), such as a method, such as can include or use receiving a mucosal surface of a bladder, superficial to a target volume within a bladder wall, at a first surface of a distal region of a device; and inserting a longitudinal portion of a therapy delivery element into the target volume at a substantially uniform distance from the first surface of the device; and providing therapy to the target volume using the therapy delivery element.

Example 26A can include or use, or can optionally be combined with the subject matter of one or any combination of Examples 1A through 25A to optionally include or use the providing therapy to the target volume including providing therapy to the target volume at a substantially uniform distance from and along the first surface of the device.

Example 27A can include or use, or can optionally be combined with the subject matter of one or any combination of Examples 1A through 26A to optionally include or use the providing therapy to the target volume including providing therapy to the target volume while retaining the mucosal surface of the bladder wall superficial to the target volume substantially intact.

Example 28A can include or use, or can optionally be combined with the subject matter of one or any combination of Examples 1A through 27A to optionally include or use the inserting the therapy delivery element into the target volume a substantially uniform distance from the first surface of the device includes at least 2 mm from the first surface of the device.

Example 29A can include or use, or can optionally be combined with the subject matter of one or any combination of Examples 1A through 28A to optionally include or use: grasping a portion of the mucosal surface; and conforming the mucosal surface to at least a portion of the first surface of the device.

Example 30A can include or use, or can optionally be combined with the subject matter of one or any combination of Examples 1A through 29A to optionally include or use the grasping the portion of the mucosal surface including using a suction port on or proximate to the first surface of the device.

Example 31A can include or use, or can optionally be combined with the subject matter of one or any combination of Examples 1A through 30A to optionally include or use the first surface of the device defining a first plane.

Example 32A can include or use, or can optionally be combined with the subject matter of one or any combination of Examples 1A through 31A to optionally include or use the inserting the longitudinal portion of the therapy delivery element includes inserting a first needle into the target volume at a substantially uniform distance from the first surface of the device.

Example 33A can include or use, or can optionally be combined with the subject matter of one or any combination of Examples 1A through 32A to optionally include or use the inserting the longitudinal portion of the therapy delivery element includes inserting first and second needles into the target volume at a substantially uniform distance from the first surface of the device, wherein the providing therapy to the target volume using the therapy delivery element includes delivering bipolar radio frequency (RF) energy to the target volume.

Example 34A can include or use, or can optionally be combined with the subject matter of one or any combination of Examples 1A through 33A to optionally include or use the providing therapy to the target volume including provide thermal energy to the target volume at the substantially uniform distance from and along the first surface of the device.

Example 35A can include or use, or can optionally be combined with the subject matter of one or any combination of Examples 1A through 34A to optionally include or use the providing therapy to the target volume includes to modulate at least one of a sense of urge, a sense of pressure, incontinence, frequency, nocturia, bladder capacity, or pain.

Example 36A can include or use, or can optionally be combined with the subject matter of one or any combination of Examples 1A through 35A to optionally include or use the providing therapy to the target volume including to modulate nerve traffic to or from at least a portion of the bladder.

Example 37A can include or use, or can optionally be combined with the subject matter of one or any combination of Examples 1A through 23A to optionally include or use the providing therapy to the target volume including ablating at least a portion of the target volume.

Example 38A can include or use, or can optionally be combined with the subject matter of one or any combination of Examples 1A through 37A to optionally include or use inserting a device into a bladder through a urethra; and positioning the device at a desired position within the bladder.

Example 39A can include or use, or can optionally be combined with the subject matter of one or any combination of Examples 1A through 38A to optionally include or use the positioning the device at the desired position within the bladder including positioning the device proximate to at least a portion of a trigone region of the bladder.

Example 40A can include or use, or can optionally be combined with the subject matter of one or any combination of Examples 1A through 39A to optionally include or use the positioning the device at the desired position within the bladder includes positioning the device between or below the ureteral orifices.

Example 1B can include or use subject matter (such as an apparatus, a method, a means for performing acts, or a device readable medium including instructions that, when performed by the device, can cause the device to perform acts), such as a method, such as can include or use concentrating energy delivery in non-superficial target tissue within a trigone region of a human bladder wall to modulate bladder function.

Example 2B can include or use, or can optionally be combined with the subject matter of claim 1B to optionally include or use the concentrating energy delivery including concentrating thermal energy delivery in non-superficial target tissue at a uniform distance spaced apart from a mucosal surface of the bladder wall to modulate bladder function.

Example 3B can include or use, or can optionally be combined with the subject matter of one or any combination of Examples 1B or 2B to optionally include or use the concentrating energy delivery in non-superficial target tissue including: positioning a portion of an energy delivery element in the non-superficial target tissue at a uniform distance spaced apart from the mucosal surface of the bladder wall and delivering energy to the non-superficial target tissue using the energy delivery element.

Example 4B can include or use, or can optionally be combined with the subject matter of one or any combination of Examples 1B through 3B to optionally include or use the concentrating energy delivery in non-superficial target tissue including positioning a location of each of a plurality of energy delivery elements in the non-superficial target tissue at a uniform distance spaced apart from the mucosal surface of the bladder wall and delivering energy to the non-superficial target tissue using the plurality of energy delivery elements.

Example 5B can include or use, or can optionally be combined with the subject matter of one or any combination of Examples 1B through 4B to optionally include or use the concentrating energy delivery including discharging thermal energy within the non-superficial target tissue in the trigone region of the bladder wall at a uniform distance spaced apart from a mucosal surface of the bladder wall to modulate bladder function.

Example 6B can include or use, or can optionally be combined with the subject matter of one or any combination of Examples 1B through 5B to optionally include or use retaining a mucosal surface of the bladder wall superficial to the non-superficial target tissue substantially intact while concentrating energy delivery in the non-superficial target tissue.

Example 7B can include or use, or can optionally be combined with the subject matter of one or any combination of Examples 1B through 6B to optionally include or use the retaining the mucosal surface of the bladder wall superficial to the non-superficial target tissue substantially intact while concentrating energy delivery in the non-superficial tissue including receiving a portion of the mucosal surface at a first surface of an apparatus, penetrating the mucosal surface of the bladder wall with a first energy delivery element, positioning a portion of the first energy delivery element in the non-superficial target tissue at a uniform distance spaced apart from the first surface of the apparatus, and delivering energy to the non-superficial target tissue using the first energy delivery element.

Example 8B can include or use, or can optionally be combined with the subject matter of one or any combination of Examples 1B through 7B to optionally include or use the retaining the mucosal surface of the bladder wall superficial to the non-superficial target tissue substantially intact while concentrating energy delivery in the non-superficial tissue including receiving a portion of the mucosal surface at a first surface of an apparatus, penetrating the mucosal surface of the bladder wall with a plurality of energy delivery elements, positioning a location of each of the plurality of energy delivery elements in the non-superficial target tissue at a uniform distance spaced apart from the first surface of the apparatus, and delivering energy to the non-superficial target tissue using the plurality of energy delivery elements.

Example 9B can include or use, or can optionally be combined with the subject matter of one or any combination of Examples 1B through 8B to optionally include or use the positioning portions of the first energy delivery element in the non-superficial target tissue at the uniform distance spaced apart from the first surface of the apparatus including positioning a longitudinal portion of the first energy delivery element in the non-superficial target tissue at a uniform distance spaced apart from the first surface of the apparatus.

Example 10B can include or use, or can optionally be combined with the subject matter of one or any combination of Examples 1B through 9B to optionally include or use at least partially filling a human bladder with fluid prior to the concentrating energy delivery to non-superficial target tissue within the trigone region of the bladder wall of the human bladder.

Example 11B can include or use, or can optionally be combined with the subject matter of one or any combination of Examples 1B through 10B to optionally include or use using an anesthetic injection into the trigone region of a human bladder wall to screen potential patients in a separate procedure prior to concentrating thermal energy delivery.

Example 12B can include or use, or can optionally be combined with the subject matter of one or any combination of Examples 1B through 11B to optionally include or use modulating nerve traffic to or from at least a portion of a human bladder using the concentrated energy delivery.

Example 13B can include or use, or can optionally be combined with the subject matter of one or any combination of Examples 1B through 12B to optionally include or use the concentrating energy delivery including modulating at least one of a sense of urinary urge, a sense of urgency, a sense of urinary pressure, urinary incontinence, urinary frequency, nocturia, bladder capacity, or pelvic pain using the concentrated energy delivery.

Example 14B can include or use, or can optionally be combined with the subject matter of one or any combination of Examples 1B through 13B to optionally include or use the concentrating energy delivery including delivering energy to non-superficial target tissue within the bladder wall between, inferior to, or between and inferior to the ureteral orifices.

Example 15B can include or use, or can optionally be combined with the subject matter of one or any combination of Examples 1B through 14B to optionally include or use the concentrating energy delivery including delivering energy to a pelvic nerve within the trigone region of the bladder wall.

Example 16B can include or use, or can optionally be combined with the subject matter of one or any combination of Examples 1B through 15B to optionally include or use the concentrating energy delivery including ablating the non-superficial target tissue within the trigone region of the bladder wall using the concentrated energy delivery.

Example 17B can include or use, or can optionally be combined with the subject matter of one or any combination of Examples 1B through 16B to optionally include or use the concentrating energy delivery including concentrating radio frequency (RF) energy in the non-superficial target tissue.

Example 18B can include or use, or can optionally be combined with the subject matter of one or any combination of Examples 1B through 17B to optionally include or use the concentrating energy delivery including delivering at least one of microwave energy, laser energy, cryo energy, ultrasound energy, or electrocautery energy to the non-superficial target tissue.

Example 19B can include or use, or can optionally be combined with the subject matter of one or any combination of Examples 1B through 18B to optionally include or use receiving a portion of a mucosal surface at a first surface of an apparatus and positioning a portion of an energy delivery element in the non-superficial target tissue and delivering energy to the non-superficial target tissue using the portion of the energy delivery element to concentrate energy delivery in the non-superficial target tissue.

Example 20B can include or use, or can optionally be combined with the subject matter of one or any combination of Examples 1B through 19B to optionally include or use the receiving the portion of the mucosal surface including applying suction to grasp and conform the portion of the mucosal surface to at least a portion of the first surface of the apparatus.

Example 21B can include or use, or can optionally be combined with the subject matter of one or any combination of Examples 1B through 20B to optionally include or use the concentrating energy delivery in non-superficial target tissue including positioning a first needle electrode in the non-superficial target tissue at locations that are a uniform distance spaced apart from the first surface of the apparatus and delivering energy to the non-superficial target tissue using the first needle electrode.

Example 22B can include or use, or can optionally be combined with the subject matter of one or any combination of Examples 1B through 21B to optionally include or use the concentrating energy delivery in non-superficial target tissue including positioning first and second needle electrodes in the non-superficial target tissue, the first surface of the apparatus defining a first plane, at least portions of the first and second needle electrodes defining a second plane, the second plane a uniform distance spaced apart from the first plane and delivering energy to the non-superficial target tissue using the first and second needle electrodes positioned in the non-superficial target tissue.

Example 23B can include or use, or can optionally be combined with the subject matter of one or any combination of Examples 1B through 22B to optionally include or use the positioning the longitudinal portion of the energy delivery element including positioning first and second needle electrodes in a bipolar configuration in the non-superficial target tissue, and the concentrating energy delivery including delivering bipolar energy to the non-superficial target tissue using the first and second needle electrodes.

Example 24B can include or use, or can optionally be combined with the subject matter of one or any combination of Examples 1B through 23B to optionally include or use at least partially denervating the non-superficial target tissue using the concentrated energy delivery.

Example 25B can include or use subject matter (such as an apparatus, a method, a means for performing acts, or a device readable medium including instructions that, when performed by the device, can cause the device to perform acts), such as a method, such as can include or use concentrating thermal energy delivery in non-superficial target tissue within a trigone region of a human bladder wall at a uniform distance spaced apart from a mucosal surface of the bladder wall to modulate bladder function and at least partially denervating the non-superficial target tissue using the concentrated thermal energy delivery, the concentrating thermal energy delivery to the non-superficial target tissue including retaining the mucosal surface of the bladder wall superficial to the non-superficial target tissue substantially intact.

Example 26B can include or use, or can optionally be combined with the subject matter of one or any combination of Examples 1B through 25B to optionally include or use applying suction to grasp and conform a portion of the mucosal surface to at least a portion of a first surface of an apparatus and positioning a portion of an energy delivery element in the non-superficial target tissue and delivering thermal energy using the portion of the energy delivery element to concentrate thermal energy delivery in the non-superficial target tissue.

Example 27B can include or use, or can optionally be combined with the subject matter of one or any combination of Examples 1B through 26B to optionally include or use the concentrating thermal energy delivery in non-superficial target tissue including positioning a portion of an energy delivery element in the non-superficial target tissue at a uniform distance spaced apart from the mucosal surface of the bladder wall and delivering energy to the non-superficial target tissue using the energy delivery element.

Example 28B can include or use, or can optionally be combined with the subject matter of one or any combination of Examples 1B through 27B to optionally include or use the concentrating thermal energy delivery in non-superficial target tissue including positioning a location of each of a plurality of energy delivery elements in the non-superficial target tissue at a uniform distance spaced apart from the mucosal surface of the bladder wall and delivering energy to the non-superficial target tissue using the plurality of energy delivery elements.

Example 29B can include or use, or can optionally be combined with the subject matter of one or any combination of Examples 1B through 28B to optionally include or use the concentrating thermal energy delivery including concentrating radio frequency (RF) energy in the non-superficial target tissue within the trigone region of the bladder wall and ablating the non-superficial target tissue using the concentrated thermal energy delivery.

Example 30B can include or use subject matter (such as an apparatus, a method, a means for performing acts, or a device readable medium including instructions that, when performed by the device, can cause the device to perform acts), such as a method, such as can include or use applying suction to grasp and conform a portion of a mucosal surface of a trigone region of a human bladder wall to a first surface of an apparatus, positioning portions of first and second energy delivery elements in non-superficial target tissue within a trigone region of the bladder wall, and discharging thermal energy within the non-superficial target tissue in the trigone region of the bladder wall at a uniform distance spaced apart from the first surface of the apparatus using the portions of the first and second energy delivery elements to modulate bladder function.

Example 31B can include or use, or can optionally be combined with the subject matter of one or any combination of Examples 1B through 30B to optionally include or use the discharging thermal energy within the non-superficial target tissue including retaining the mucosal surface of the bladder wall superficial to the non-superficial target tissue substantially intact.

Example 32B can include or use, or can optionally be combined with the subject matter of one or any combination of Examples 1B through 31B to optionally include or use at least partially filling a human bladder with fluid before applying suction to grasp and conform a portion of the mucosal surface of the trigone region of the bladder wall of the human bladder to the first surface of the apparatus.

Example 33B can include or use, or can optionally be combined with the subject matter of one or any combination of Examples 1B through 32B to optionally include or use at least partially denervating the non-superficial target tissue using the discharged thermal energy and modulating bladder function using the at least partial denervation, modulating bladder function including modulating at least one of a sense of urinary urge, a sense of urgency, a sense of urinary pressure, urinary incontinence, urinary frequency, nocturia, bladder capacity, or pelvic pain.

Example 34B can include or use, or can optionally be combined with the subject matter of one or any combination of Examples 1B through 33B to optionally include or use the discharging thermal energy including discharging radio frequency (RF) energy within the non-superficial target tissue in the trigone region of the bladder wall and ablating the non-superficial target tissue using the concentrated thermal energy delivery, the positioning portions of the first and second energy delivery elements including positioning first and second needle electrodes in the non-superficial target tissue in a bipolar configuration, and the discharging RF energy within the non-superficial target tissue including discharging bipolar RF energy to the non-superficial target tissue using the first and second needle electrodes.

Example 35B can include or use subject matter (such as an apparatus, a method, a means for performing acts, or a device readable medium including instructions that, when performed by the device, can cause the device to perform acts), such as an apparatus, such as can include or use means for concentrating energy delivery in non-superficial target tissue within a trigone region of a human bladder wall to modulate bladder function.

Example 36B can include or use, or can optionally be combined with the subject matter of one or any combination of Examples 1B through 35B to optionally include or use an elongated shaft sized and shaped to be inserted into a human urethra, the means for concentrating energy delivery including a distal region coupled to the elongated shaft, the distal region sized and shaped to be inserted into a human bladder through the urethra, a first energy delivery element configured to deliver thermal energy concentrated in the non-superficial target tissue within the trigone region of the bladder wall of the human bladder.

Example 37B can include or use, or can optionally be combined with the subject matter of one or any combination of Examples 1B through 36B to optionally include or use the distal region including a first surface defining a first plane and a suction port at the first surface, the first surface configured to receive a portion of a mucosal surface of the trigone region of the bladder wall using the suction port, the first energy delivery element a uniform distance spaced apart from the first plane, the first energy delivery element configured to deliver thermal energy concentrated to the non-superficial target tissue within the trigone region of the bladder wall to modulate bladder function while retaining the mucosal surface of the bladder wall superficial to the non-superficial target tissue substantially intact, and the first surface laterally accessible on at least two sides.

Example 1C can include or use subject matter (such as an apparatus, a method, a means for performing acts, or a device readable medium including instructions that, when performed by the device, can cause the device to perform acts), such as an apparatus, such as can include or use an elongated shaft sized and shaped to be inserted into a human urethra, a distal region coupled to the elongated shaft, the distal region sized and shaped to be inserted into a human bladder through the urethra, the distal region having a first surface defining a first plane, the first surface configured to receive a portion of a mucosal surface of a trigone region of a bladder wall of the bladder, and first and second energy delivery elements defining a second plane, the second plane a uniform distance spaced apart from the first plane, the first and second energy delivery elements configured to deliver energy to non-superficial target tissue within a trigone region of a bladder wall to modulate bladder function, the first surface laterally accessible on at least two sides.

Example 2C can include or use, or can optionally be combined with the subject matter Examples 1C to optionally include or use the first surface including a suction port, and the first surface is configured to receive the portion of the mucosal surface of the trigone region of the bladder wall using the suction port.

Example 3C can include or use, or can optionally be combined with the subject matter of one or any combination of Examples 1C through 2C to optionally include or use the first and second energy delivery elements extendable in the second plane and configured to deliver energy to the non-superficial target tissue within the trigone region of the bladder wall while retaining a mucosal surface of the bladder wall superficial to the non-superficial target tissue substantially intact.

Example 4C can include or use, or can optionally be combined with the subject matter of one or any combination of Examples 1C through 3C to optionally include or use locations along the first and second energy delivery elements that define the second plane.

Example 5C can include or use, or can optionally be combined with the subject matter of one or any combination of Examples 1C through 4C to optionally include or use the first surface coupled on one side to the elongated shaft and is laterally accessible about the remainder of the first surface to receive the mucosal surface of the trigone region of the bladder wall.

Example 6C can include or use, or can optionally be combined with the subject matter of one or any combination of Examples 1C through 5C to optionally include or use the first surface having a length extending longitudinally from the elongated shaft, the length of the first surface greater than a width of the first surface by a factor of at least 3.

Example 7C can include or use, or can optionally be combined with the subject matter of one or any combination of Examples 1C through 6C to optionally include or use the first and second energy delivery elements including longitudinal portions configured to be disposed in the non-superficial target tissue at the uniform distance spaced apart from the first surface of the distal region, the longitudinal portions of the first and second energy delivery elements defining the second plane, and a length of the longitudinal portions of the first and second energy delivery elements greater than the uniform distance spaced apart from the first surface of the distal region by a factor of at least 3.

Example 8C can include or use, or can optionally be combined with the subject matter of one or any combination of Examples 1C through 7C to optionally include or use the first and second energy delivery elements are configured to deliver energy to non-superficial target tissue within the trigone region of a bladder wall to modulate bladder at least one of a sense of urinary urge, a sense of urgency, a sense of urinary pressure, urinary incontinence, urinary frequency, nocturia, bladder capacity, or pelvic pain.

Example 9C can include or use, or can optionally be combined with the subject matter of one or any combination of Examples 1C through 8C to optionally include or use the first and second energy delivery elements are configured to deliver radio frequency (RF) energy to the non-superficial target tissue within the trigone region of the bladder wall to modulate bladder function.

Example 10C can include or use, or can optionally be combined with the subject matter of one or any combination of Examples 1C through 9C to optionally include or use the first and second energy delivery elements configured to modulate nerve traffic to or from the trigone region of the bladder wall using the delivered energy.

Example 11C can include or use, or can optionally be combined with the subject matter of one or any combination of Examples 1C through 10C to optionally include or use the first and second energy delivery elements including thermal energy delivery elements configured to discharge thermal energy within the non-superficial target tissue in the trigone region of the bladder wall.

Example 12C can include or use, or can optionally be combined with the subject matter of one or any combination of Examples 1C through 11C to optionally include or use the first and second energy delivery elements configured to ablate the non-superficial target tissue within the trigone region of the bladder wall to modulate bladder function.

Example 13C can include or use, or can optionally be combined with the subject matter of one or any combination of Examples 1C through 12C to optionally include or use the first and second energy delivery elements including at least one of a microwave energy source, a laser energy source, a cryo energy source, an ultrasound energy source, or a monopolar or bipolar electrocautery energy source.

Example 14C can include or use subject matter (such as an apparatus, a method, a means for performing acts, or a device readable medium including instructions that, when performed by the device, can cause the device to perform acts), such as a method, such as can include or use inserting an elongated shaft into a human urethra, the elongated shaft sized and shaped for insertion into the urethra, inserting a distal region coupled to the elongated shaft into a human bladder through the urethra, the distal region sized and shaped for insertion into the bladder through the urethra, the distal region having a first surface defining a first plane, the first surface laterally accessible on at least two sides, receiving a portion of a mucosal surface of a trigone region of a bladder wall of the bladder at the first surface of the distal region, locating first and second energy delivery elements in a second plane, the second plane a uniform distance spaced apart from the first plane, and delivering energy to non-superficial target tissue within a trigone region of a bladder wall to modulate bladder function using the first and second energy delivery elements.

Example 15C can include or use, or can optionally be combined with the subject matter of one or any combination of Examples 1C through 14C to optionally include or use the delivering energy to the non-superficial target tissue including concentrating energy delivery in the non-superficial target tissue within the trigone region of the bladder wall to modulate bladder function while retaining the mucosal surface of the bladder wall superficial to the non-superficial target tissue substantially intact, and the retaining the mucosal surface of the bladder wall superficial to the non-superficial target tissue substantially intact including receiving the portion of the mucosal surface at the first surface of the distal region, penetrating the mucosal surface of the bladder wall with the first and second energy delivery elements, positioning portions of the first and second energy delivery elements in the non-superficial target tissue in the second plane, and delivering energy to the non-superficial target tissue using the first and second energy delivery elements.

Example 16C can include or use, or can optionally be combined with the subject matter of one or any combination of Examples 1C through 15C to optionally include or use at least partially filling the bladder with fluid before delivering energy to the non-superficial target tissue.

Example 17C can include or use, or can optionally be combined with the subject matter of one or any combination of Examples 1C through 16C to optionally include or use the delivering energy to the non-superficial target tissue including delivering bipolar energy to the non-superficial target tissue using the first and second energy delivery elements and at least partially denervating the non-superficial target tissue using the delivered bipolar energy.

Example 18C can include or use, or can optionally be combined with the subject matter of one or any combination of Examples 1C through 17C to optionally include or use the receiving the portion of the mucosal surface including using a suction port at the first surface to grasp and conform the portion of the mucosal surface to at least a portion of the first surface of the apparatus.

Example 19C can include or use, or can optionally be combined with the subject matter of one or any combination of Examples 1C through 18C to optionally include or use using an anesthetic injection into the trigone region of a human bladder wall to screen potential patients in a separate procedure prior to concentrating thermal energy delivery.

Example 20C can include or use subject matter (such as an apparatus, a method, a means for performing acts, or a device readable medium including instructions that, when performed by the device, can cause the device to perform acts), such as an apparatus, such as can include or use an elongated shaft sized and shaped to be inserted into a human urethra, a distal region coupled to the elongated shaft, the distal region sized and shaped to be inserted into a human bladder through the urethra, and an energy delivery element configured to deliver energy to non-superficial target tissue within a trigone region of a bladder wall of the bladder to modulate bladder function, the energy delivery element having a treatment length greater than a width of the distal region by a factor of at least 3.

Example 21C can include or use, or can optionally be combined with the subject matter of one or any combination of Examples 1C through 20C to optionally include or use the energy delivery element having a treatment length greater than the width of the distal region by a factor of at least 4.

Example 22C can include or use, or can optionally be combined with the subject matter of one or any combination of Examples 1C through 21C to optionally include or use the energy delivery element configured to deliver energy to non-superficial target tissue at a uniform distance spaced apart from the mucosal surface of the bladder to modulate bladder function.

Example 23C can include or use, or can optionally be combined with the subject matter of one or any combination of Examples 1C through 22C to optionally include or use the energy delivery element including first and second energy delivery elements configured to deliver energy to non-superficial target tissue.

Example 24C can include or use, or can optionally be combined with the subject matter of one or any combination of Examples 1C through 23C to optionally include or use the distal region including a first surface configured to receive a portion of the mucosal surface of the trigone region of the bladder wall, the first surface defining a first plane, the energy delivery element a uniform distance spaced apart from the first plane, a length of the distal region greater than the uniform distance spaced apart from the first plane by a factor of at least 3.

Example 25C can include or use, or can optionally be combined with the subject matter of one or any combination of Examples 1C through 24C to optionally include or use the distal region including a first surface configured to receive a portion of the mucosal surface of the trigone region of the bladder wall, the energy delivery element including a longitudinal portion configured to be disposed in the non-superficial target tissue at a uniform distance spaced apart from the first surface of the distal region to deliver energy to the non-superficial target tissue while retaining the mucosal surface of the bladder wall superficial to the non-superficial target tissue substantially intact.

Example 26C can include or use, or can optionally be combined with the subject matter of one or any combination of Examples 1C through 25C to optionally include or use the first surface including a suction port configured to grasp and conform the portion of the mucosal surface to at least a portion of the first surface.

Example 27C can include or use, or can optionally be combined with the subject matter of one or any combination of Examples 1C through 26C to optionally include or use the energy delivery element including first and second needle electrodes having longitudinal portions configured to deliver energy along the treatment length.

Example 28C can include or use subject matter (such as an apparatus, a method, a means for performing acts, or a device readable medium including instructions that, when performed by the device, can cause the device to perform acts), such as an apparatus, such as can include or use an elongated shaft sized and shaped to be inserted into a human urethra, a distal region coupled to the elongated shaft, the distal region sized and shaped to be inserted into a human bladder through the urethra, and an energy delivery element configured to deliver energy to non-superficial target tissue within a trigone region of a bladder wall of the bladder to modulate bladder function, the distal region including a first surface configured to receive a portion of a mucosal surface of the trigone region of the bladder wall, the energy delivery element including longitudinally distributed locations configured to be disposed in the non-superficial target tissue at a uniform distance spaced apart from the first surface of the distal region, and a length spanned by the longitudinally distributed locations greater than the uniform distance spaced apart from the first surface of the distal region by a factor of at least 3.

Example 29C can include or use, or can optionally be combined with the subject matter of one or any combination of Examples 1C through 28C to optionally include or use the energy delivery element including a longitudinal portion, the longitudinally distributed locations of the energy delivery element disposed along the longitudinal portion of the energy delivery element, the longitudinal portion configured to be disposed in the non-superficial target tissue at the uniform distance spaced apart from the first surface of the distal region, and a length of the longitudinal portion greater than the uniform distance spaced apart from the first surface of the distal region by a factor of at least 3.

Example 30C can include or use, or can optionally be combined with the subject matter of one or any combination of Examples 1C through 29C to optionally include or use the energy delivery element including first and second energy delivery elements having longitudinal portions configured to deliver energy to the non-superficial target tissue.

Example 31C can include or use, or can optionally be combined with the subject matter of one or any combination of Examples 1C through 30C to optionally include or use the length spanned by the longitudinally distributed locations greater than the uniform distance spaced apart from the first surface of the distal region by a factor of 3-6.

Example 32C can include or use, or can optionally be combined with the subject matter of one or any combination of Examples 1C through 31C to optionally include or use the length spanned by the longitudinally distributed locations greater than the uniform distance spaced apart from the first surface of the distal region by a factor of at least 4.

Example 33C can include or use, or can optionally be combined with the subject matter of one or any combination of Examples 1C through 32C to optionally include or use length spanned by the longitudinally distributed locations greater than a width of the first surface by a factor of at least 3.

Example 34C can include or use, or can optionally be combined with the subject matter of one or any combination of Examples 1C through 33C to optionally include or use the energy delivery element including a plurality of energy delivery elements corresponding to respective longitudinally distributed location, each of the plurality of energy delivery elements configured to be positioned in the non-superficial target tissue from the first surface.

Example 35C can include or use, or can optionally be combined with the subject matter of one or any combination of Examples 1C through 34C to optionally include or use the first surface including a suction port configured to grasp and conform the portion of the mucosal surface to at least a portion of the first surface.

Example 36C can include or use, or can optionally be combined with the subject matter of one or any combination of Examples 1C through 35C to optionally include or use the energy delivery element configured to deliver energy to the non-superficial target tissue within the trigone region of the bladder wall to modulate bladder function while retaining a mucosal surface of the bladder wall superficial to the non-superficial target tissue substantially intact.

Example 37C can include or use, or can optionally be combined with the subject matter of one or any combination of Examples 1C through 36C to optionally include or use the length spanned by the longitudinally distributed locations greater than the uniform distance spaced apart from the first surface of the distal region by a factor of 4-5.

The above detailed description includes references to the accompanying drawings, which form a part of the detailed description. The drawings show, by way of illustration, specific embodiments in which the invention can be practiced. These embodiments are also referred to herein as "examples." In the event of inconsistent usages between this document and any documents incorporated by reference, the usage in this document controls.

While one or more of the figures described herein reference the female anatomy, the systems and methods disclosed herein are equally applicable to the male anatomy, and the use of female anatomy should not be construed as limiting the invention in any way.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. In other examples, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A method of modulating bladder function, the method comprising:
    maintaining needle electrodes of an energy delivery device within bladder wall tissue using the energy delivery device positioned in a vagina of a patient; and
    activating the needle electrodes within the bladder wall tissue while the energy delivery device is positioned in the vagina to disrupt afferent nerve signals associated with bladder function by applying ablative thermal energy from the needle electrodes of the energy delivery device to a targeted portion of the bladder wall tissue at a selected depth from an inner wall of the vagina.

2. The method of claim 1, wherein the applying ablative thermal energy from the needle electrodes of the energy delivery device to the targeted portion of the bladder wall tissue at the selected depth from the inner wall of the vagina comprises applying RF energy using the needle electrodes to the portion of the bladder wall tissue.

3. The method of claim 1, wherein the applying ablative thermal energy from the needle electrodes of the energy delivery device to the targeted portion of the bladder wall tissue at the selected depth from the inner wall of the vagina comprises ablating afferent nerves emanating from the bladder.

4. The method of claim 1, wherein the applying ablative thermal energy from the needle electrodes of the energy delivery device to the targeted portion of the bladder wall tissue at the selected depth from the inner wall of the vagina comprises applying the ablative thermal energy to targeted nerves proximate a trigone region of the bladder.

5. The method of claim 1, wherein proximal portions of the needle electrodes include an electrically insulative coating such that the ablative thermal energy does not flow between the proximal portions of the needle electrodes.

6. The method of claim 1, wherein the energy delivery device is advanced into the vagina while steering the energy delivery device.

7. The method of claim 1, wherein the needle electrodes comprise a pair of needle electrodes that are oriented parallel to one another.

8. The method of claim 1, wherein the needle electrodes consist of a pair of needle electrodes that are oriented parallel to one another.

9. The method of claim 1, further comprising penetrating the needle electrodes through a mucosal surface of the vagina.

10. The method of claim 1, wherein the method treats an overactive bladder condition of the patient.

11. The method of claim 1, wherein said applying ablative thermal energy from the needle electrodes of the energy delivery device to the targeted portion of the bladder wall tissue at the selected depth from the inner wall of the vagina comprises applying the ablative thermal energy to targeted nerves in a trigone region of the bladder.

12. The method of claim 1, further comprising, visualizing, using an imaging system, a position of the energy delivery device within the vagina.

13. The method of claim 1, further comprising, after the energy delivery device is positioned in the vagina, deploying the needle electrodes.

14. The method of claim 1, wherein the targeted portion of the bladder wall tissue is non-superficial tissue of the bladder.

15. The method of claim 1, wherein said applying ablative thermal energy from the needle electrodes of the energy delivery device to the targeted portion of the bladder wall tissue at the selected depth from the inner wall of the vagina comprises avoiding damage to the superficial mucosal layer of the bladder wall tissue.

* * * * *